United States Patent [19]
Taveras

[11] Patent Number: 6,051,582
[45] Date of Patent: *Apr. 18, 2000

[54] COMPOUNDS USEFUL FOR INHIBITION OF FARNESYL PROTEIN TRANSFERASE

[75] Inventor: Arthur G. Taveras, Rockaway, N.J.

[73] Assignee: Schering Corporation, Kenilworth, N.J.

[*] Notice: This patent is subject to a terminal disclaimer.

[21] Appl. No.: 09/094,802

[22] Filed: Jun. 15, 1998

Related U.S. Application Data

[60] Provisional application No. 60/049,952, Jun. 17, 1997.

[51] Int. Cl.⁷ .................... A61K 31/445; C07D 401/14; C07D 221/16

[52] U.S. Cl. ............................................. 514/290; 546/93

[58] Field of Search ................... 514/290; 546/93

[56] References Cited

U.S. PATENT DOCUMENTS

| | | | |
|---|---|---|---|
| 4,826,853 | 5/1989 | Piwinski et al. | 514/290 |
| 5,089,496 | 2/1992 | Piwinski et al. | 514/253 |
| 5,151,423 | 9/1992 | Piwinski et al. | 514/254 |
| 5,393,890 | 2/1995 | Syoji et al. | 546/80 |
| 5,661,152 | 8/1997 | Bishop et al. | 514/254 |
| 5,672,611 | 9/1997 | Doll et al. | 514/325 |
| 5,684,013 | 11/1997 | Afonso et al. | 514/290 |
| 5,696,121 | 12/1997 | Bishop et al. | 514/254 |
| 5,700,806 | 12/1997 | Doll et al. | 514/290 |
| 5,703,090 | 12/1997 | Afonso et al. | 514/290 |
| 5,712,280 | 1/1998 | Doll et al. | 514/253 |
| 5,714,609 | 2/1998 | Bishop et al. | 546/93 |
| 5,719,148 | 2/1998 | Bishop et al. | 514/228.2 |
| 5,721,236 | 2/1998 | Bishop et al. | 514/255 |
| 5,728,703 | 3/1998 | Bishop et al. | 514/254 |
| 5,807,853 | 9/1998 | Bishop | 514/228.2 |
| 5,861,395 | 1/1999 | Taveras | 514/232.8 |

FOREIGN PATENT DOCUMENTS

| | | |
|---|---|---|
| 0270818 | 6/1988 | European Pat. Off. . |
| 0 341 860 | 11/1989 | European Pat. Off. . |
| 396083 | 11/1990 | European Pat. Off. . |
| 0495484 | 7/1992 | WIPO . |
| WO95/10515 | 4/1995 | WIPO . |
| WO95/10516 | 4/1995 | WIPO . |
| WO95/15949 | 6/1995 | WIPO . |
| WO96/30018 | 10/1996 | WIPO . |
| WO96/30362 | 10/1996 | WIPO . |
| WO96/30363 | 10/1996 | WIPO . |
| WO96/31477 | 10/1996 | WIPO . |
| WO96/31478 | 10/1996 | WIPO . |
| WO97/23478 | 7/1997 | WIPO . |

OTHER PUBLICATIONS

Bishop et al., The Journal of Biological Chemistry, vol. 270, No. 15, pp.30611–30618 (1995).

Njoroge et al., Bioorganic & Medicinal Chemistry Letters, vol. 6, No.24, pp.2977–2982 (1996).

Khosravi–Far R et al. Cell Growth & Differentiation. 3, 461–9, Jul. 1992.

Primary Examiner—Evelyn Mei Huang
Attorney, Agent, or Firm—Henry C. Jeanette

[57] ABSTRACT

Novel compounds of the formula:

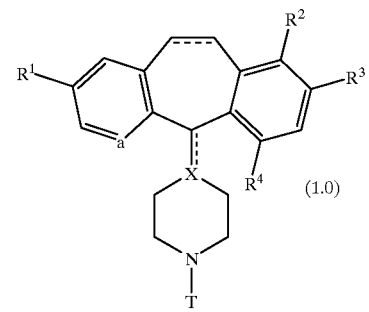

or a pharmaceutically acceptable salt or solvate thereof, wherein:

a represents N or NO⁻;

$R^1$ and $R^3$ are the same or different and each represents halo;

$R^2$ and $R^4$ are each independently selected from H and halo, provided that at least one of $R^2$ and $R^4$ is H;

each dotted line (---) represents an optional bond;

X is N, C when the optional bond to X is present, or CH when the optional bond to X is absent;

T is a substituent selected from:

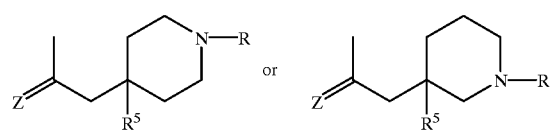

Z represents O or S;

R represents —$SO_2R^{10}$;

$R^5$ represents alkyl, aryl, arylalkyl, heteroaryl, heteroarylalkyl, cycloalkyl, $OR^{12}$, $NR^{12}H$, SH, $SR^{12}$, $SOR^{12}$ (where $R^{12}$ is not H), or $SO_2R^{12}$ (where $R^{12}$ is not H); and each $R^{10}$ independently represents H, alkyl, aryl, or aralkyl;

$R^{11}$ is alkyl, aryl, aralkyl, heteroaryl or heterocycloalkyl;

$R^{12}$ is selected from H, alkyl, aryl, aralkyl, heteroaryl, heteroarylalkyl, or heterocycloalkyl. Also disclosed are methods of inhibiting farnesyl protein transferase and methods for treating tumor cells.

19 Claims, No Drawings

COMPOUNDS USEFUL FOR INHIBITION OF FARNESYL PROTEIN TRANSFERASE

REFERENCE TO RELATED APPLICATIONS

This application claims the benefit of U.S. Provisional Application Ser. No. 60/049,952 filed Jun. 17, 1997.

BACKGROUND

WO 95/10516, published Apr. 20, 1995 discloses tricyclic compounds useful for inhibiting farnesyl protein transferase.

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

This invention provides compounds useful for the inhibition of farnesyl protein transferase (FPT). The compounds of this invention are represented by the formula:

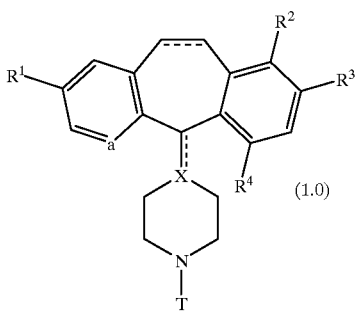

(1.0)

or a pharmaceutically acceptable salt or solvate thereof, wherein:

a represents N or NO$^-$;

$R^1$ and $R^3$ are the same or different and each represents halo;

$R^2$ and $R^4$ are each independently selected from H and halo, provided that at least one of $R^2$ and $R^4$ is H;

each dotted line (---) represents an optional bond;

X is N, C when the optional bond to X is present, or CH when the optional bond to X is absent;

T is a substituent selected from:

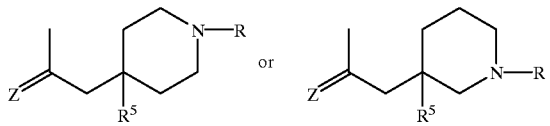

Z represents O or S;

R represents —C(O)N($R^{10}$)$_2$, —CH$_2$C(O)N($R^{10}$)$_2$, —SO$_2R^{10}$, —SO$_2$N($R^{10}$)$_2$, —C(O)$R^{11}$, —C(O)—O—$R^{11}$, alkyl, aryl, aralkyl, cycloalkyl, heterocycloalkyl or heteroaryl;

$R^5$ represents alkyl, aryl, aralkyl, heteroaryl, heteroarylalkyl, cycloalkyl, O$R^{12}$, N$R^{12}$H, S$R^{12}$, SO$R^{12}$ (where $R^{12}$ is not H), or SO$_2R^{12}$ (where $R^{12}$ is not H); and each $R^{10}$ independently represents H, alkyl, aryl, or aralkyl (e.g., benzyl);

$R^{11}$ is alkyl, aryl, aralkyl, heteroaryl or heterocycloalkyl;

$R^{12}$ is selected from H, alkyl, aryl, aralkyl, heteroaryl, heteroarylalkyl, or heterocycloalkyl.

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras. Thus, this invention further provides a method of inhibiting farnesyl protein transferase, (e.g., ras farnesyl protein transferase) in mammals, especially humans, by the administration of an effective amount of the compounds of formula 1.0. The administration of the compounds of this invention to patients, to inhibit farnesyl protein transferase, is useful in the treatment of the cancers described below.

This invention provides a method for inhibiting or treating the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor growth by administering an effective amount of the compounds of formula 1.0 to a mammal (e.g., a human) in need of such treatment. In particular, this invention provides a method for inhibiting or treating the growth of tumors expressing an activated Ras oncogene by the administration of an effective amount of the above described compounds. Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, breast cancer and prostate cancer.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount of the compounds of formula 1.0 to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the compounds of formula 1.0.

The compounds of formula 1.0 useful in the methods of this invention inhibit or treat the abnormal growth of cells. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:

MH+-represents the molecular ion plus hydrogen of the molecule in the mass spectrum;

Et (or ET)-represents ethyl ($C_2H_5$);

alkyl-represents straight and branched carbon chains that contain from one to twenty carbon atoms, preferably one to six carbon atoms;

halo-represents fluoro, chloro, bromo and iodo;

cycloalkyl-represents saturated carbocyclic rings branched or unbranched of from 3 to 20 carbon atoms, preferably 3 to 7 carbon atoms;

heterocycloalkyl-represents a saturated, branched or unbranched carbocylic ring containing from 3 to 15 carbon atoms, preferably from 4 to 6 carbon atoms, which carbocyclic ring is interrupted by 1 to 3 hetero groups selected from —O—, —S— or —$NR^{12}$- (suitable heterocycloalkyl groups including 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, etc.);

aryl (including the aryl portion of aryloxy and aralkyl)-represents a carbocyclic group containing from 6 to 15 carbon atoms and having at least one aromatic ring (e.g., aryl is a phenyl (Ph) ring), with all available substitutable carbon atoms of the carbocyclic group being intended as possible points of attachment, said carbocyclic group being optionally substituted (e.g., 1 to 3) with one or more of halo, alkyl, hydroxy, alkoxy, phenoxy, $CF_3$, amino, alkylamino, dialkylamino, —$COOR^{10}$ or —$NO_2$; and heteroaryl-represents cyclic groups, optionally substituted with $R^{10}$, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms, e.g., triazolyl, 2-, 3- or 4-pyridyl or pyridyl N-oxide (optionally substituted with $R^3$ and $R^4$), wherein pyridyl N-oxide can be represented as:

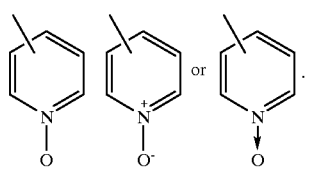

The following solvents and reagents are referred to herein by the abbreviations indicated: ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); 1-(3-dimethylaminopropyl)-3-ethyl carbodiimide hydrochloride (DEC), trimethylsilyl (TMS); m-chloro-peroxybenzoic acid (MCPBA); lithium diisopropylamide (LDA); dimethylsulfoxide (DMSO); sodium borohydride ($NaBH_4$); diisobutylaluminum hydride(DIBAL); and 4-methylmorpholine (NMM).

The positions in the tricyclic ring system are:

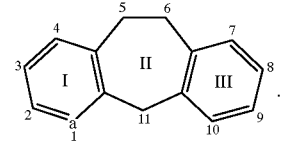

Those skilled in the art will also appreciate that the S and R stereochemistry for the C-11 position of the tricyclic ring when X is CH or N is as follows:

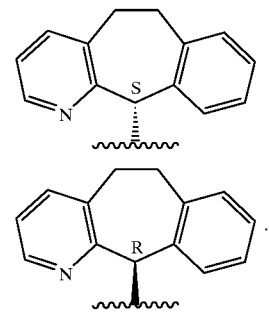

Preferred halo atoms for $R^1$, $R^2$, $R^3$, and $R^4$ in formula 1.0 are selected from: Br, Cl or I, with Br and Cl being preferred.

Compounds of formula 1.0 include compounds of the formula

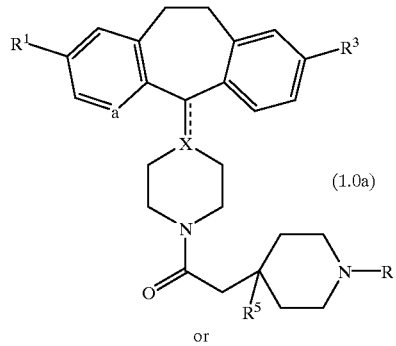

(1.0a)

or

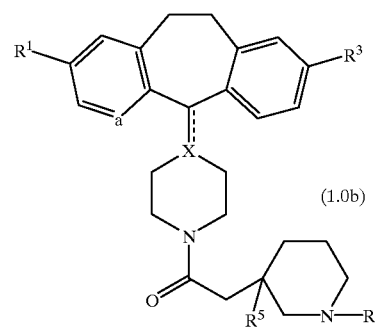

(1.0b)

wherein $R^1$ and $R^3$ are the same or different halo and a, X, $R^5$, R and the dotted lines are as defined above. Preferably, for these dihalo compounds, $R^1$ and $R^3$ are independently selected from Br or Cl, and more preferably $R^1$ is Br and $R^3$ is Cl. Preferably, X is CH or N, with CH being more preferred.

Compounds of formula 1.0 include compounds of formulas 1.1a and 1.1b and formulas 1.2a and 1.2b:

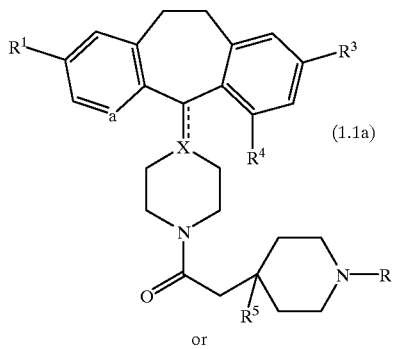
(1.1a)

or

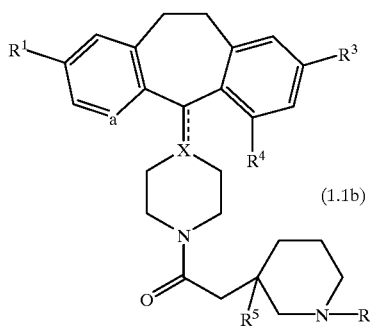
(1.1b)

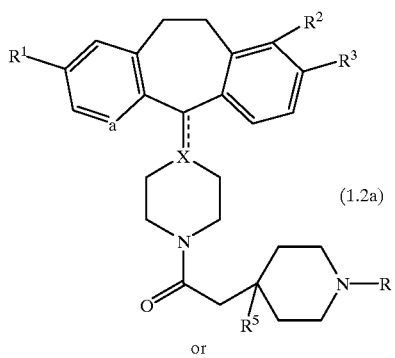
(1.2a)

or

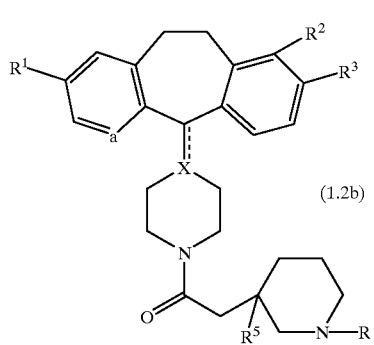
(1.2b)

wherein $R^1$, $R^3$ and $R^4$ in formulas 1.1a and 1.1b are halo, and $R^1$, $R^2$ and $R^3$ in formula 1.2a and 1.2b are halo and wherein a, X, R, $R^5$, and the dotted lines are as defined above. Compounds of formulas 1.1a and 1.1b are preferred.

Preferably, in formulas 1.1a and 1.1b, $R^1$ is Br, $R^3$ is Cl, and $R^4$ is halo. More preferably, in formulas 1.1a and 1.1b, $R^1$ is Br, $R^3$ is Cl, and $R^4$ is Br.

Preferably, in formulas 1.2a and 1.2b, $R^1$ is Br, $R^2$ is halo, and $R^3$ is Cl. More preferably, in formulas 1.2a and 1.2b, $R^1$ is Br, $R^2$ is Br, and $R^3$ is Cl.

Preferably, for compounds of formulas 1.1a, 1.1b, 1.2a and 1.2b, X is CH or N. For compounds of formulas 1.1a and 1.1b, X is preferably CH.

Preferably, for the compounds of this invention, the optional bond between positions 5 and 6 (i.e., C5–C6) in the tricyclic system is absent.

Also, preferably, for the compounds of this invention, substituent a in ring I represents N and the optional double bond at position 11 is absent.

Those skilled in the art will appreciate that compounds of formula 1.0 include compounds of formulas 1.3 and 1.4:

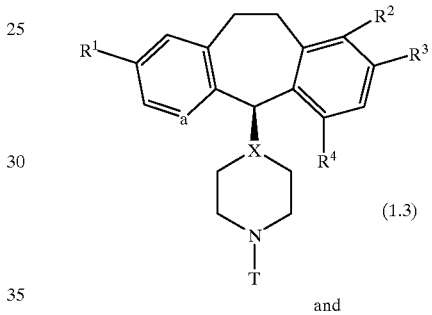
(1.3)

and

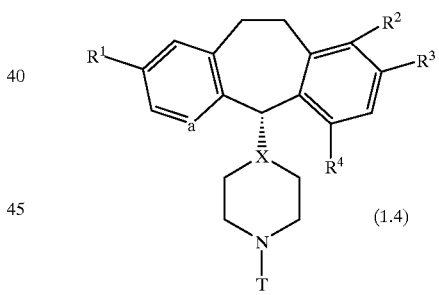
(1.4)

wherein X is CH or N, with compounds of 1.3 being preferred for compounds of formula 1.1, and with compounds of formula 1.4 being preferred for compounds of formula 1.2.

The preferred T groups for use in the present invention include:

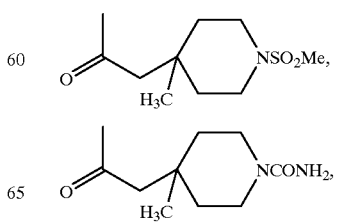

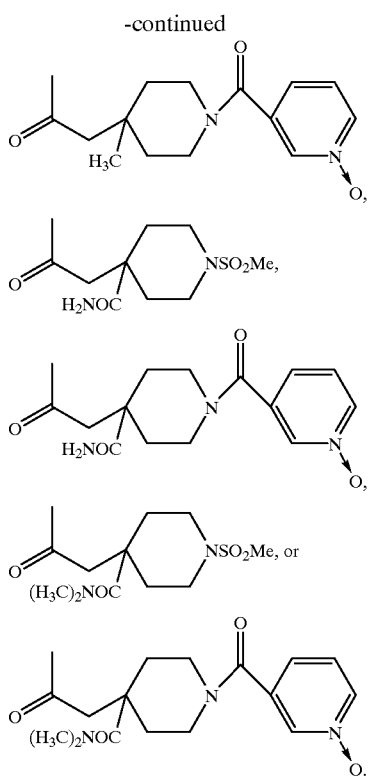

Certain compounds of the invention may exist in different isomeric (e.g., enantiomers and diastereoisomers) forms. The invention contemplates all such isomers both in pure form and in admixture, including racemic mixtures. Enol forms are also included.

Certain compounds of formula 1.0 will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of formula 1.0 also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Intermediates useful in the preparation of compounds of the invention may be prepared according to the procedures described in WO 95/10516 published Apr. 20, 1995, in WO 96/30363 published Oct. 3, 1996, in U.S. Pat. No. 5,151,423 and by the methods described below.

Compounds of the invention can be prepared according to the reaction:

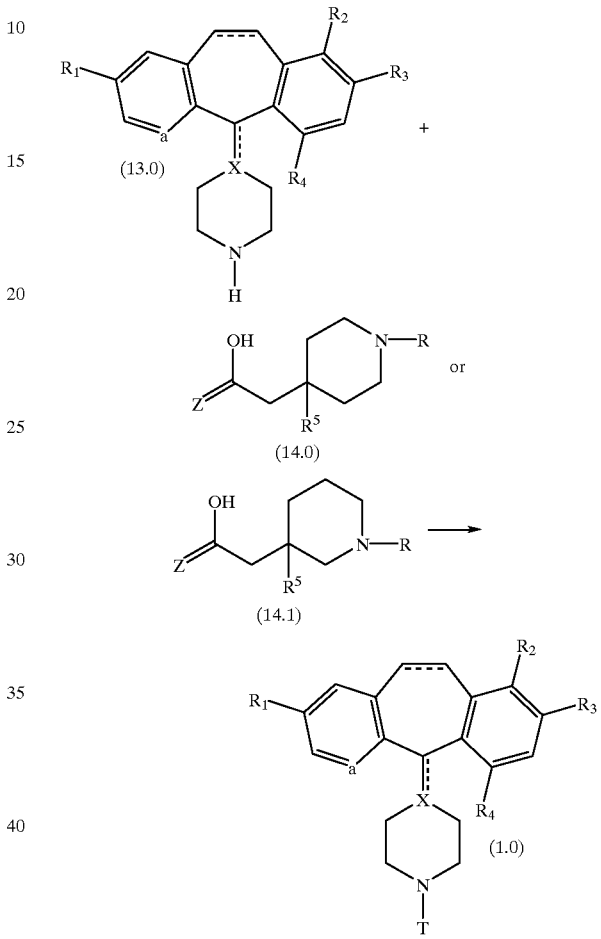

In the reaction, the carboxylic acid (14.0 or 14.1) (which may also be an alkali metal salt such as a lithium salt of 14.0 or 14.1 or an acid halide of the acid) is coupled to the tricyclic amine (13.0) using amide bond forming conditions well known to those skilled in the art. The substituents are as defined for formula 1.0. For example, carbodiimide coupling methods (e.g., DEC) can be used. For example, the carboxylic acid (14.0 or 14.1) can be reacted with the tricyclic amine (13.0) using DEC/HOBT/NMM in DMF at about 25° C. for a sufficient period of time, e.g., about 18 hours, to produce a compound of formula 1.0.

The carboxylic acids (14.0 and 14.1) are prepared by methods well known in the art.

The general procedures described below can be used to prepare the compounds of formulas 14.0 and 14.1 above. In the schematics shown below, the 4-piperdinyl group is illustrated, but a 3-piperdinyl group can be employed in essentially the same manner. The compound of formula 16.0 is commercially available from Aldrich. The 3-piperdinyl analog of formula 16.0 is described in A. Tercinet, Bull. Soc. Chem. France 11, p. 500 (1944).

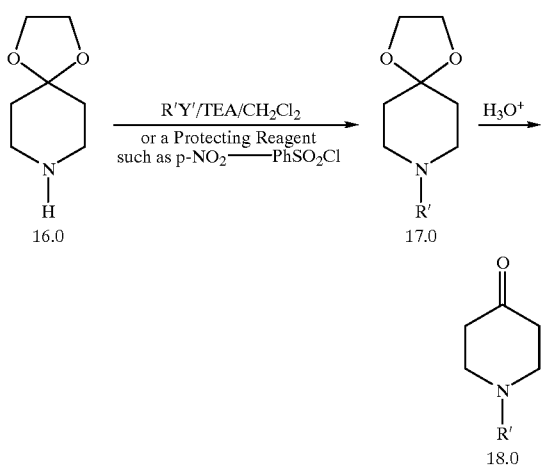

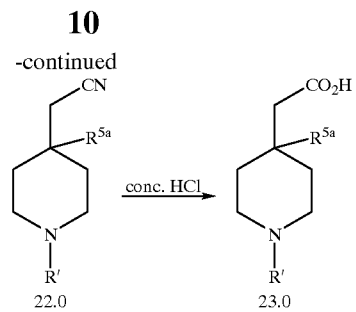

When R is group R', wherein R' is —SO$_2$R$^{10}$, —SO$_2$N(R$^{10}$)$_2$, alkyl, aryl, aralkyl, cycloalkyl, heterocycloalkyl or heteroaryl, the R' group can be placed on the piperdinyl nitrogen in the first step, i.e., by reaction of formula 16.0 with a compound R'Y', where Y' is halo such as Cl, Br, or I in the case of SO$_2$R$^{10}$, —SO$_2$N(R$^{10}$)$_2$, alkyl, aralkyl, cycloalkyl, heterocycloalkyl or heteroaryl, and Y' is I in the case of aryl (using a Pd catalyst and tetrabutyl ammonium bromide in DMF).

Alternatively, R' can be a protecting group (Pro) such as a p-nitrobenzenesulfonate or benzyl group, which can be placed on the piperdinyl nitrogen in the first step by reaction of p-nitrobenzenesulfonyl or benzyl chloride in the presence of TEA in CH$_2$Cl$_2$ with the compound of formula 16.0 or its 3-piperdinyl analog. In this case, R' will represent Pro in formulas 17.0 and 18.0 above. If R' is a protecting group (Pro), it can be replaced with a suitable R group as described later below.

To prepare compounds of formulas 14.0 and 14.1 wherein R$^5$ is R$^{5a}$ which represents alkyl, aryl, aralkyl, heteroaryl, heteroarylalkyl or cycloalkyl, the following reaction scheme can be employed, wherein R' is as described above:

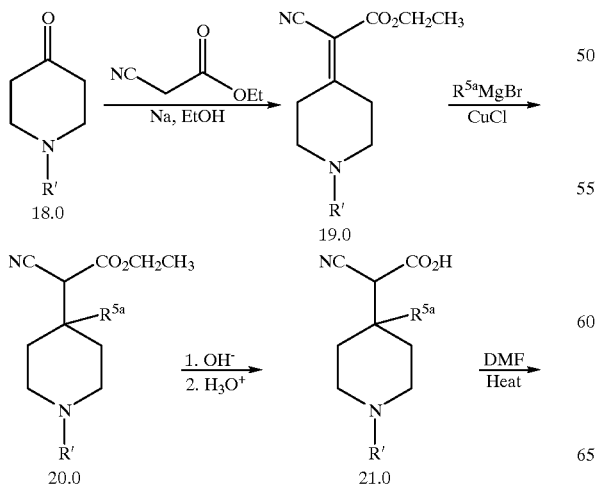

If R' is a protecting group (Pro), it can be replaced with a suitable R group as described later below. These reactions are illustrated in Preparative Examples 10–16 below. The protecting group in 23.0 where R' is Pro can be removed by catalytic hydrogenation in the case of Pro=benzyl or by treatment with NaSMe in the case of p-nitrobenzenesulfonyl.

To prepare compounds of formulas 14.0 and 14.1 wherein R$^5$ is SR$^{12}$, SOR$^{12}$ or SO$_2$R$^{12}$, the following reaction scheme can be employed, wherein R' is as described above:

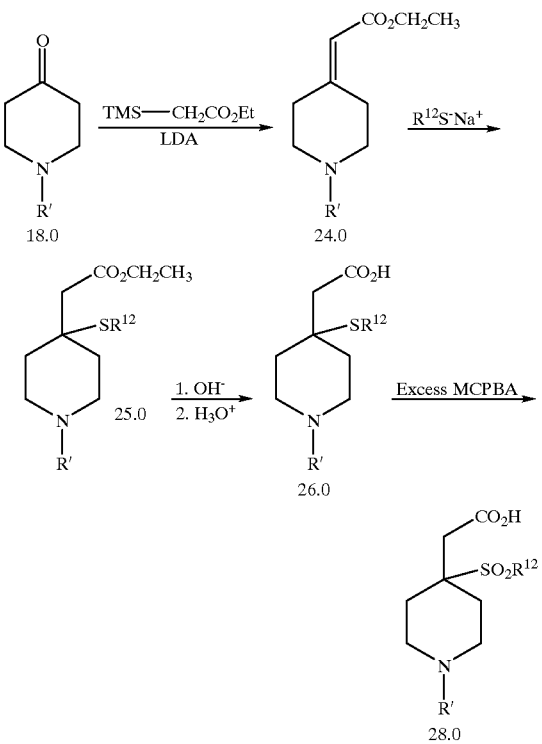

In the first step, treatment of compound 18.0 with the anion of ethyl trimethylsilyl acetate affords 24.0, followed by Michael addition of the sodium thiolate affords 25.0, the ester of which can be saponified with aqueous sodium hydroxide to afford 26.0 following protonation with aqueous acid. Oxidation of 26.0 with excess MCPBA affords 28.0. For compounds wherein R$^5$ is SOR$^{12}$, the group SR$^{12}$ in formula 26.0 above can be oxidized by using 1 equivalent of MCPBA in CH$_2$Cl$_2$ at room temperature.

To prepare compounds of formulas 14.0 and 14.1 wherein R$^5$ is OR$^{12}$, the following reaction scheme can be employed, wherein R' is as described above:

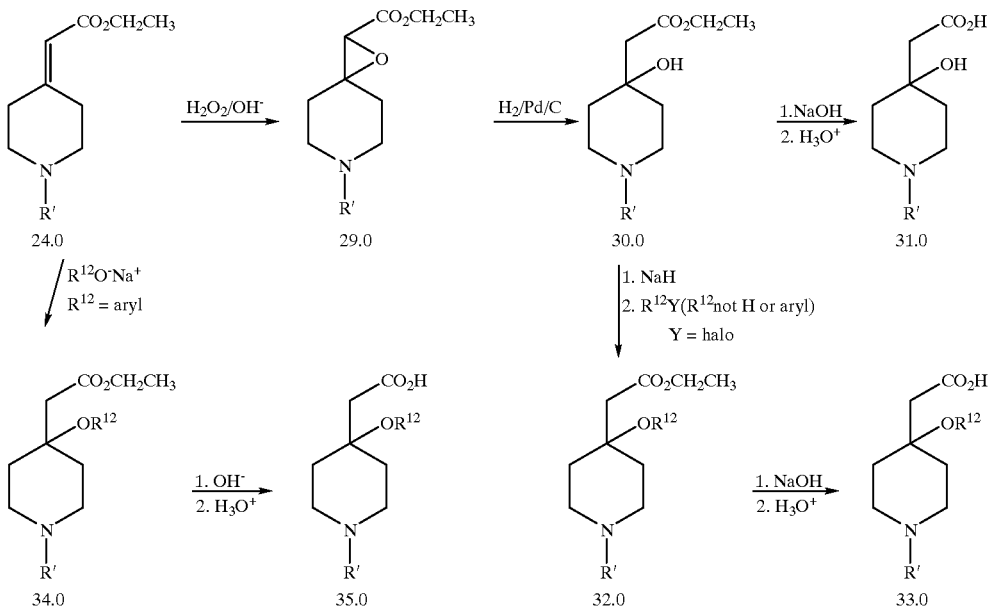

Treatment of 24.0 with basic hydrogen peroxide affords epoxide 29.0, which can be reduced using catalytic hydrogenation to give 30.0. Hydrolysis of the ester in 30.0 yields 31.0 following protonation. Treatment of 30.0 with sodium hydride and a suitable alkylating agent affords 32.0, which can be saponified and protonated similarly as above. Alternatively, treatment of 24.0 with the sodium salt of $R^{12}OH$ affords 34.0, which when saponified and protonated gives 35.0.

To prepare compounds of formulas 14.0 and 14.1 wherein $R^5$ is $NHR^{12}$, the following reaction scheme can be employed, wherein R' is as described above:

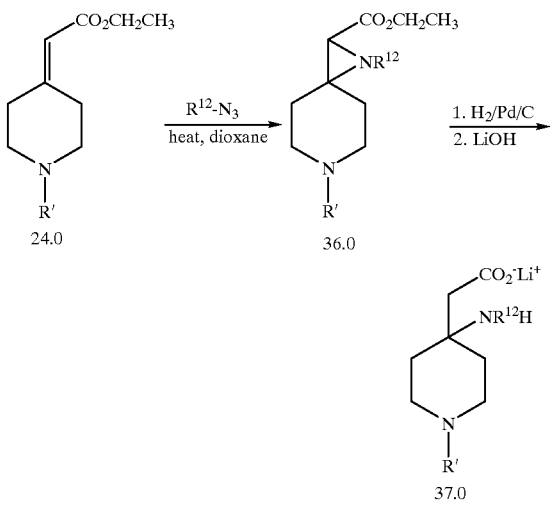

[3+2] Dipolar cycloaddition of 24.0 with $R^{12}$azide in refluxing dioxane gives 36.0, which can be reduced using catalytic hydrogenation followed by saponification with LiOH to give 37.0.

Compounds of Formula 13.0 can be prepared from compounds of formula 13.0a:

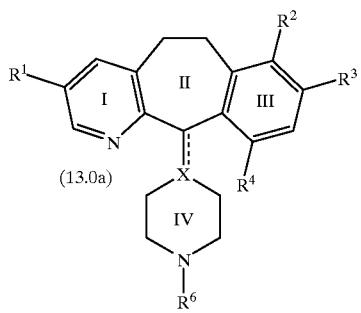

(13.0a)

wherein $R^6$ is H, alkyl, carboalkoxy or any other group that can be converted into a group T. The compounds of formula 13.0a are prepared by methods known in the art, for example, by methods disclosed in WO 95/10516 published Apr. 20, 1995, in WO 96/30363 published Oct. 3, 1996, in U.S. Pat. No. 5,151,423 and by the methods described below. Compounds of Formula 13.0a wherein X is C (when the double bond is present) or CH and the C-3 position of the pyridine ring in the tricyclic structure is substituted by bromo (i.e., $R^1$ is Br) can also be prepared by a procedure comprising the following steps:

(a) reacting an amide of the formula

wherein $R^{5b}$ is hydrogen and $R^{6b}$ is $C_1$–$C_6$ alkyl, aryl or heteroaryl; $R^{5b}$ is $C_1$–$C_6$ alkyl, aryl or heteroaryl and $R^{6b}$ is hydrogen; $R^{5b}$ and $R^{6b}$ are independently selected from the group consisting of $C_1$–$C_6$ alkyl and aryl; or $R^{5b}$ and $R^{6b}$, together with the nitrogen to which they are attached, form a ring comprising 4 to 6 carbon atoms or comprising 3 to 5 carbon atoms and one hetero moiety selected from the group consisting of —O— and —NR$^{9b}$—, wherein R$^{9b}$ is H, C$_1$–C$_6$ alkyl or phenyl;

with a compound of the formula

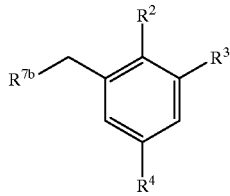

wherein R$^2$, R$^3$, and R$^4$ are as defined above and R$^{7b}$ is Cl or Br, in the presence of a strong base to obtain a compound of the formula

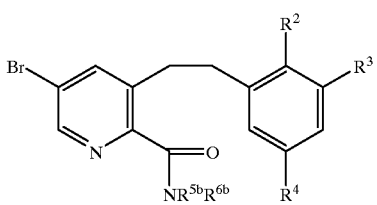

(b) reacting a compound of step (a) with
(i) POCl$_3$ to obtain a cyano compound of the formula

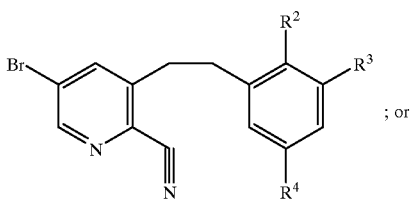; or (ii) DIBALH to obtain an aldehyde of the formula

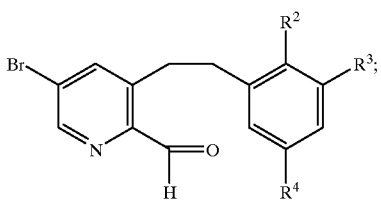

(c) reacting the cyano compound or the aldehyde with a piperidine derivative of the formula

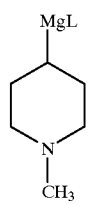

wherein L is a leaving group selected from the group consisting of Cl and Br, to obtain a ketone of the formula below:

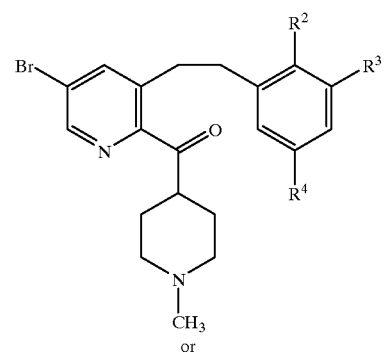

or

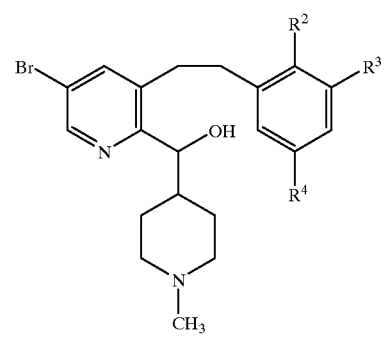

(d)(i) cyclizing the ketone with CF$_3$SO$_3$H to obtain a compound of Formula 13.0a wherein the dotted line represents a double bond and wherein R$^6$ is methyl; or (d)(ii) cyclizing the alcohol with polyphosphoric acid to obtain a compound of Formula 13.0a wherein the dotted line represents is absent (i.e., represents a single bond) and wherein R$^6$ is methyl. The R$^6$ methyl group can be converted to H by treatment with ethyl chloroformate in refluxing toluene, followed by acid hydrolysis with refluxing hydrochloric acid.

Methods for preparing compounds of Formula 13.0a disclosed in WO 95/10516, U.S. Pat. No. 5,151,423 and described below employ a tricyclic ketone intermediate. Such intermediates of the formula

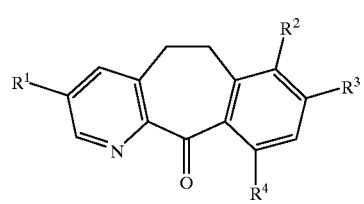

wherein R$^1$, R$^2$, R$^3$ and R$^4$ are as defined above, can be prepared by the following process comprising:

(a) reacting a compound of the formula

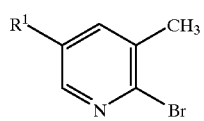

(i) with an amine of the formula NHR$^{5a}$R$^{6a}$, wherein R$^{5a}$ and R$^{6a}$ are as defined in the process above; in the presence of a palladium catalyst and carbon monoxide to obtain an amide of the formula:

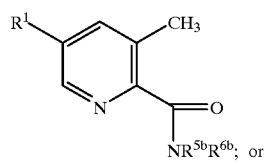

(ii) with an alcohol of the formula $R^{10b}OH$, wherein $R^{10b}$ is $C_1$–$C_6$ lower alkyl or $C_3$–$C_6$ cycloalkyl, in the presence of a palladium catalyst and carbon monoxide to obtain the ester of the formula

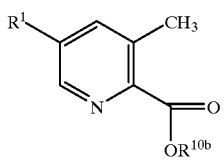

followed by reacting the ester with an amine of formula $NHR^{5b}R^{6b}$ to obtain the amide;

(b) reacting the amide with an iodo-substituted benzyl compound of the formula

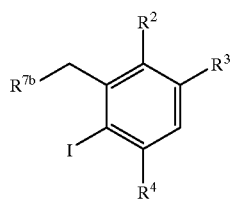

wherein $R^2$, $R^3$, $R^4$ and $R^{7b}$ are as defined above, in the presence of a strong base to obtain a compound of the formula

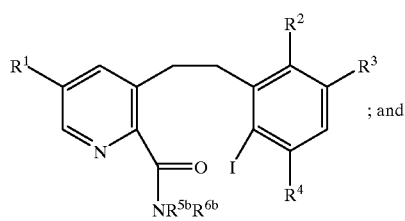

(c) cyclizing a compound of step (b) with a reagent of the formula $R^{8b}MgL$, wherein $R^{8b}$ is $C_1$–$C_8$ alkyl, aryl or heteroaryl and L is Br or Cl, provided that prior to cyclization, compounds wherein $R^{5b}$ or $R^{6b}$ is hydrogen are reacted with a suitable N-protecting group.

Compounds of the formula 13.0c below

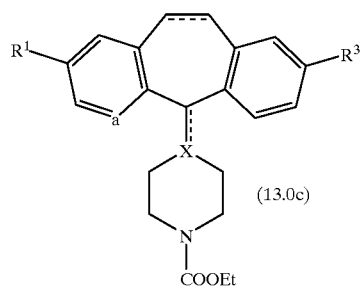

are disclosed in WO 95/10516 published Apr. 20, 1995, in WO 96/30363 published Oct. 3, 1996, and in U.S. Pat. No. 5,151,423. These compounds may be used as intermediates to prepare compound of the formula 1.0 having a double bond between positions 5 and 6 of the tricyclic ring by the reactions illustrated below.

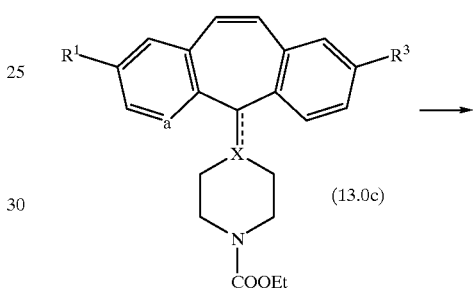

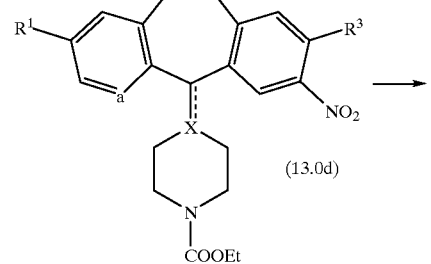

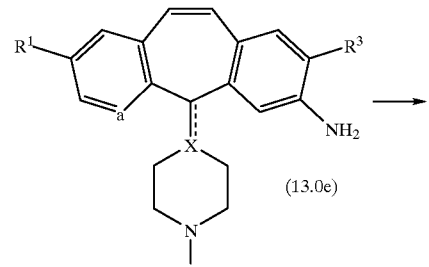

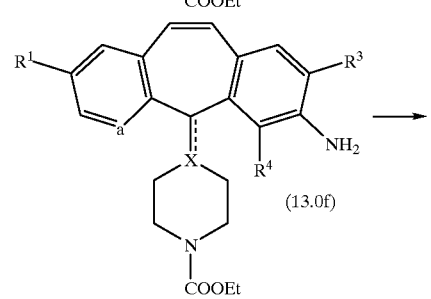

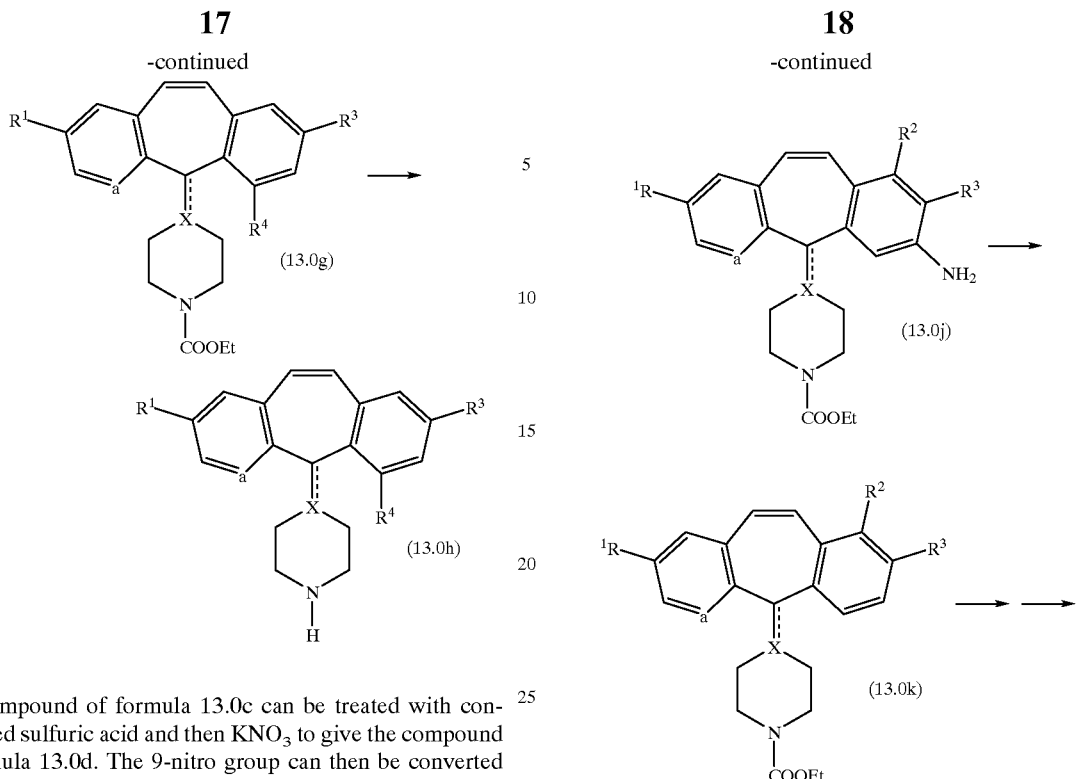

A compound of formula 13.0c can be treated with concentrated sulfuric acid and then KNO$_3$ to give the compound of formula 13.0d. The 9-nitro group can then be converted into a 9-amino group by reduction with Fe and CaCl$_2$. The compound of formula 13.0e can be halogenated in the 10-position by addition of chlorine or bromine in HOAc. The 10-iodo compound can be prepared by treatment of 13.0e with iodine in ethanolic silver sulfate. The 9-amino group can be removed by treatment with t-butylnitrite, DMF and heat to give a compound of formula 13.0g, which can be treated with concentrated HCl and heat to give the desired compound of formula 13.0h.

Compounds of formula 13.0e above can also be used to prepare compounds of formula 13.0 wherein R$^2$ is halo and there is a double bond between the 5 and 6-positions of the tricyclic ring by the reaction scheme described below:

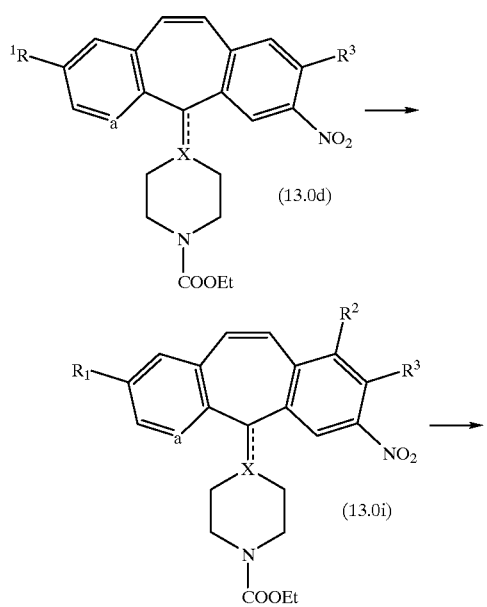

The compound of formula 13.0e is treated with concentrated sulfuric acid, cooled and then treated with 1,3-dihalo-5,5-dimethyl-hydroantoin or other appropriate halogenating agent. The product of formula 13.0i is reduced with CaCl$_2$ and Fe to give the 7-halo-9-amino compound of formula 13.0j. The 9-amino group can be removed by treatment with NaNO$_2$ and concentrated HCl and then H$_3$PO$_2$. The product of formula 13.0m can be treated with concentrated HCl to produce the desired intermediate of formula 13.0m.

The compounds of formulas 13.0h and 13.0n wherein there is a double bond at the 11-position and X is C can also be used to prepare compounds of formula below by treatment with CH$_3$CN/H$_2$O and then NaIO$_4$ and RuO$_2$. Reduction of the ketone with sodium borohydride in methanol followed by treatment with thionyl chloride and then piperazine gives an intermediate of formula 13.0p below:

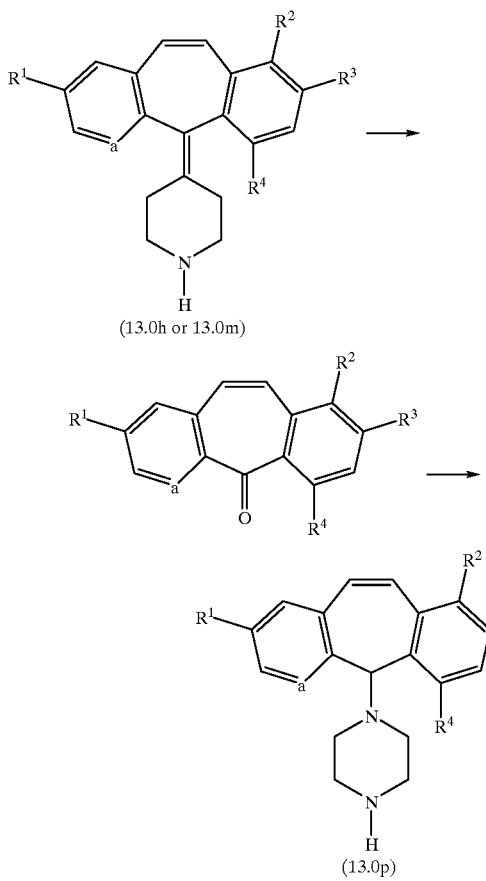

(13.0h or 13.0m)

(13.0p)

Compounds of Formula 1.0, wherein substituent a is NO (Ring I) and X is C or CH, can be made from compounds of Formula 13.0a using procedures well known to those skilled in the art. For example the compound of Formula 13.0a can be reacted with m-chloroperoxybenzoic acid in a suitable organic solvent, e.g., dichloromethane (usually anhydrous) or methylene chloride, at a suitable temperature, to produce a compound of Formula 13.0b

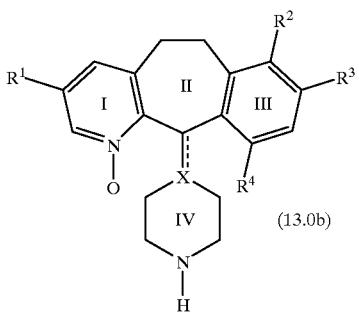

(13.0b)

Generally, the organic solvent solution of Formula 13.0a is cooled to about 0° C. before the m-chloroperoxybenzoic acid is added. The reaction is then allowed to warm to room temperature during the reaction period. The desired product can be recovered by standard separation means. For example, the reaction mixture can be washed with an aqueous solution of a suitable base, e.g., saturated sodium bicarbonate or NaOH (e.g., 1N NaOH), and then dried over anhydrous magnesium sulfate. The solution containing the product can be concentrated in vacuo. The product can be purified by standard means, e.g., by chromatography using silica gel (e.g., flash column chromatography).

Alternatively, compounds of Formula 1.0, wherein substituent a is NO and X is C or CH, can be made from compounds of Formula 1.0, wherein substituent a is N, by the m-chloroperoxybenzoic acid oxidation procedure described above.

Also, alternatively, the compounds of Formula 1.0, wherein substituent a is NO and X is C or CH, can be made from tricyclic ketone compounds

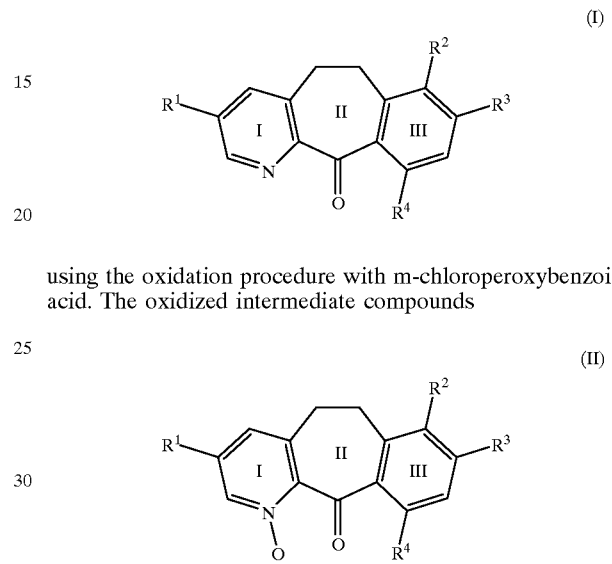

using the oxidation procedure with m-chloroperoxybenzoic acid. The oxidized intermediate compounds are then reacted by methods known in the art to produce compounds of the invention.

Those skilled in the art will appreciate that the oxidation reaction can be conducted on racemic mixtures and the isomers can then be separated by know techniques, or the isomers can be separated first and then oxidized to the corresponding N-oxide.

Those skilled in the art will appreciate that it is preferable to avoid an excess of m-chloroperoxybenzoic acid when the oxidation reaction is carried out on the compounds having a C-11 double bond to piperidine Ring IV. In these reactions an excess of m-chloroperoxybenzoic acid can cause epoxidation of the C-11 double bond.

(+)-Isomers of compounds of Formula 13.0a, wherein X is CH and $R^6$ is H, can be prepared with high enantioselectivity by using a process comprising enzyme catalyzed transesterification. Preferably, a racemic compound of Formula 13.0a, wherein X is C, $R^6$ is H, the double bond is present and $R^4$ is not H, is reacted with an enzyme such as Toyobo LIP-300 and an acylating agent such as trifluoroethyl isobutyrate; the resultant (+)-amide is then hydrolyzed, for example by refluxing with an acid such as $H_2SO_4$, to obtain the corresponding optically enriched (+)-isomer wherein X is CH and $R^3$ is not H. Alternatively, a racemic compound of Formula 13.0a, wherein X is C, $R^6$ is H, the double bond is present and $R^4$ is not H, is first reduced to the corresponding racemic compound of Formula 13.0a wherein X is CH and then treated with the enzyme (Toyobo LIP-300) and acylating agent as described above to obtain the (+)-amide, which is hydrolyzed to obtain the optically enriched (+)-isomer.

Compounds of the invention, wherein a is NO and X is N, can be prepared from the tricyclic ketone (II) described above. Ketone (II) can be converted to the corresponding C-11 hydroxy compound which in turn can be converted to the corresponding C-11 chloro compound

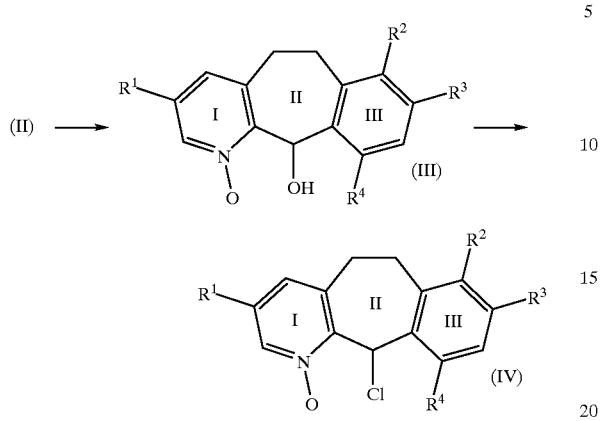

and (IV) can then be reacted with piperazine to produce the intermediate

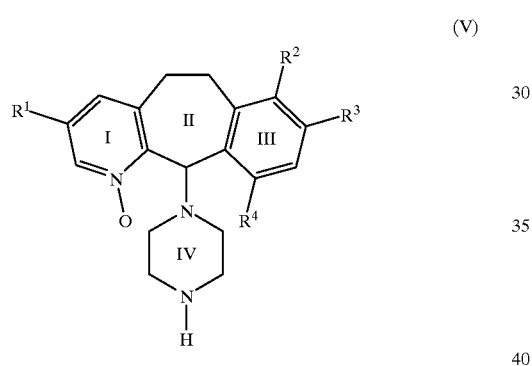

Intermediate (V) can then be reacted with the reagents, using techniques well known in the art, which will provide the desired compound.

Compounds of formula 1.0 wherein Z is S can be prepared from compounds of formula 1.0 wherein Z is O by treatment with a suitable sulfur transfer reagent such as Lawsson's reagent.

Compounds of the invention having asymmetric carbons (e.g., compounds of the invention wherein X is CH or N have an asymmetric carbon at the C-11 position of the tricyclic ring) can be separated into enantiomers by techniques known in the art, e.g., by chiral salt resolution or by chiral HPLC.

Compounds useful in this invention are exemplified by the following examples, which should not be construed to limit the scope of the disclosure.

PREPARATIVE EXAMPLE 1

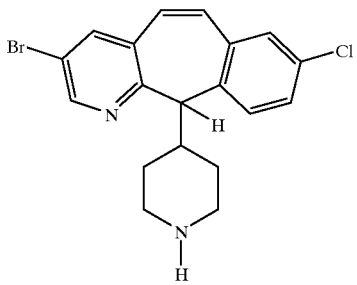

Step A:

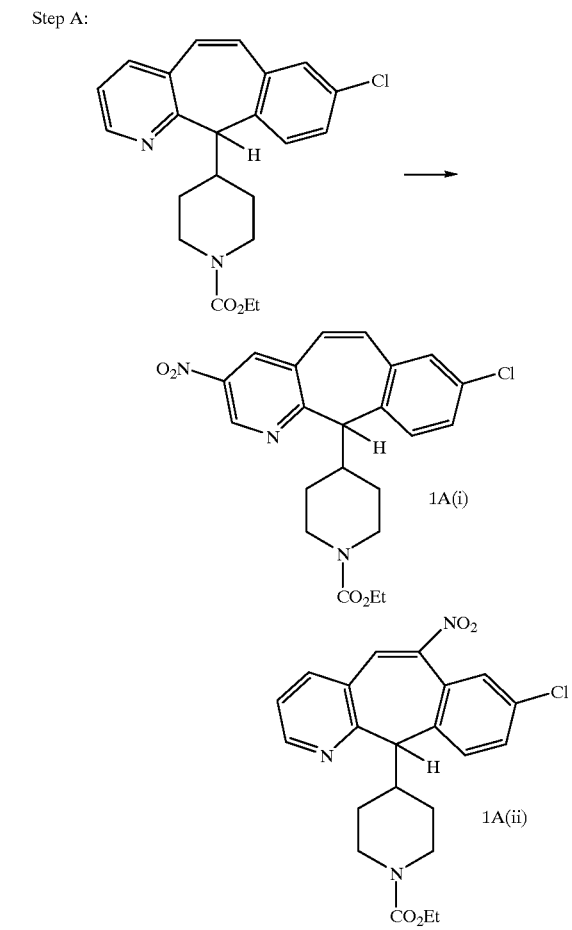

Combine 14.95 g (39 mmol) of 8-chloro-11-(1-ethoxy-carbonyl-4-piperidinyl)-11H-benzo[5,6]cyclohepta[1,2-b]pyridine and 150 mL of $CH_2Cl_2$, then add 13.07 g (42.9 mmol) of $(nBu)_4NNO_3$ and cool the mixture to 0° C. Slowly add (dropwise) a solution of 6.09 mL (42.9 mmol) of TFAA in 20 mL of $CH_2Cl_2$ over 1.5 hours. Keep the mixture at 0° C. overnight, then wash successively with saturated $NaHCO_3$ (aqueous), water and brine. Dry the organic solution over $Na_2SO_4$, concentrate in vacuo to a residue and chromatograph the residue (silica gel, EtOAc/hexane gradient) to give 4.32 g and 1.90 g of the two product compounds 1A(i) and 1A(ii), respectively. Mass Spec. for compound 1A(i): $MH^+$=428.2. Mass Spec. for compound 1A(ii): $MH^+$=428.3.

Step B:

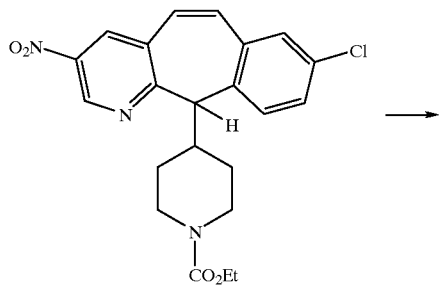

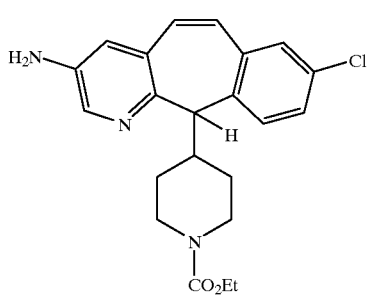

Combine 22.0 g (51.4 mmol) of the product 1A(i) from Step A, 150 mL of 85% EtOH (aqueous), 25.85 g (0.463 mole) of Fe powder and 2.42 g (21.8 mmol) of $CaCl_2$, and heat at reflux overnight. Add 12.4 g (0.222 mole) of Fe powder and 1.2 g (10.8 mmol) of $CaCl_2$ and heat at reflux for 2 hours. Add another 12.4 g (0.222 mole) of Fe powder and 1.2 g (10.8 mmol) of $CaCl_2$ and heat at reflux for 2 hours more. Filter the hot mixture through celite®, wash the celite® with 50 mL of hot EtOH and concentrate the filtrate in vacuo to a residue. Add 100 mL of anhydrous EtOH, concentrate to a residue and chromatograph the residue (silica gel, $MeOH/CH_2Cl_2$ gradient) to give 16.47 g of the product compound.

Step C:

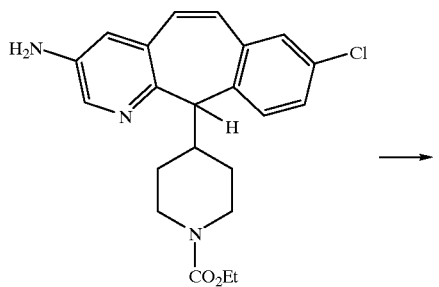

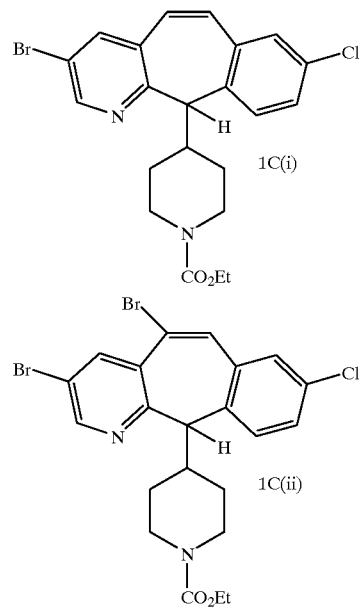

Combine 16.47 g (41.4 mmol) of the product from Step B, and 150 mL of 48% HBr (aqueous) and cool to $-3°$ C. Slowly add (dropwise) 18 mL of bromine, then slowly add (dropwise) a solution of 8.55 g (0.124 mole) of $NaNO_2$ in 85 mL of water. Stir for 45 minutes at $-3°$ to $0°$ C., then adjust to pH=10 by adding 50% NaOH (aqueous). Extract with EtOAc, wash the extracts with brine and dry the extracts over $Na_2SO_4$. Concentrate to a residue and chromatograph (silica gel, EtOAc/hexane gradient) to give 10.6 g and 3.28 g of the two product compounds 1C(i) and 1C(ii), respectively. Mass Spec. for compound 1C(i): $MH^+=461.2$. Mass Spec. for compound 1C(ii): $MH^+=539$.

Step D:

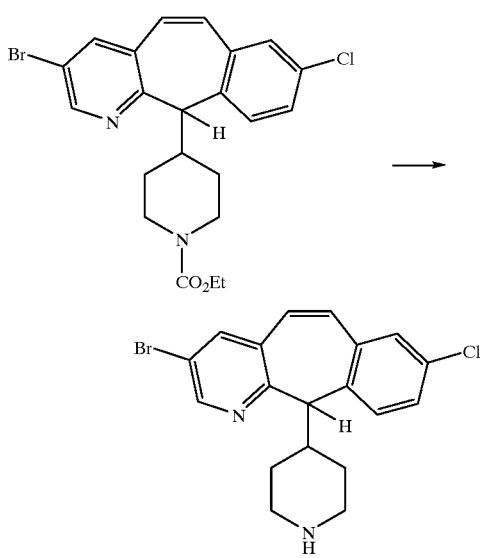

Hydrolyze the product 3C(i) of Step C by dissolving in concentrated HCl and heating to about 100° C. for @ 16 hours. Cool the mixture, the neutralize with 1 M NaOH (aqueous). Extract with $CH_2Cl_2$, dry the extracts over $MgSO_4$, filter and concentrate in vacuo to the title compound. Mass Spec.: $MH^+=466.9$.

PREPARATIVE EXAMPLE 2

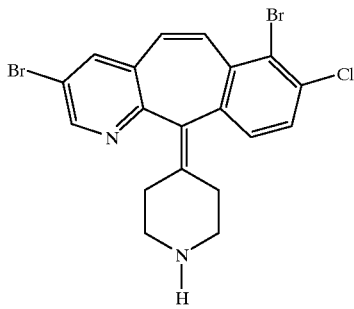

Step A:

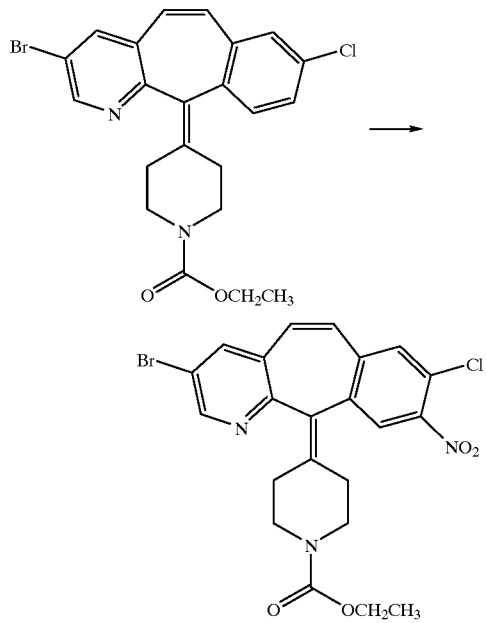

Combine 25.86 g (55.9 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 250 mL of concentrated $H_2SO_4$ at −5° C., then add 4.8 g (56.4 mmol) of $NaNO_3$ and stir for 2 hours. Pour the mixture into 600 g of ice and basify with concentrated $NH_4OH$ (aqueous). Filter the mixture, wash with 300 mL of water, then extract with 500 mL of $CH_2Cl_2$. Wash the extract with 200 mL of water, dry over $MgSO_4$, then filter and concentrate in vacuo to a residue. Chromatograph the residue (silica gel, 10% $EtOAc/CH_2Cl_2$) to give 24.4 g (86% yield) of the product. m.p.=165–167° C., Mass Spec.: $MH^+=506$ (CI). Elemental analysis: calculated-C, 52.13; H, 4.17; N, 8.29; found-C, 52.18; H, 4.51; N, 8.16.

Step B:

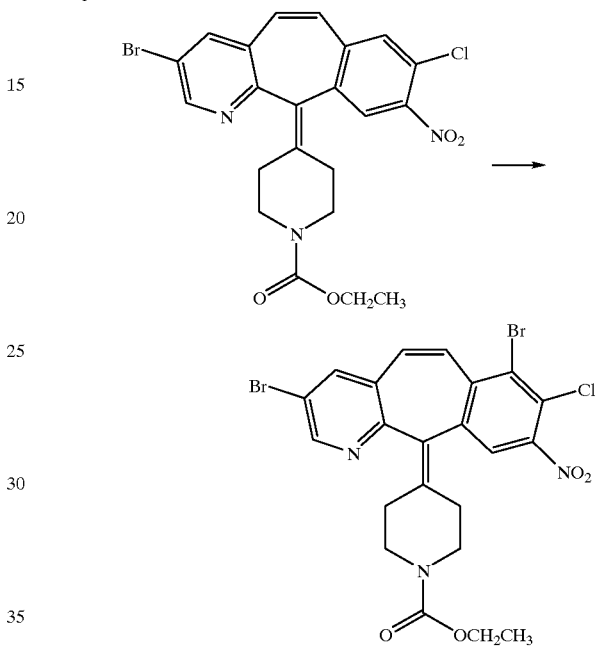

Combine 20 g (40.5 mmol) of the product of Step A and 200 mL of concentrated $H_2SO_4$ at 20° C., then cool the mixture to 0° C. Add 7.12 g (24.89 mmol) of 1,3-dibromo-5,5-dimethylhydantoin to the mixture and stir for 3 hours at 20° C. Cool to 0° C., add an additional 1.0 g (3.5 mmol) of the dibromohydantoin and stir at 20° C. for 2 hours. Pour the mixture into 400 g of ice, basify with concentrated $NH_4OH$ (aqueous) at 0° C., and collect the resulting solid by filtration. Wash the solid with 300 mL of water, slurry in 200 mL of acetone and filter to provide 19.79 g (85.6% yield) of the product. m.p.=236–237° C., Mass Spec.: $MH^+=584$ (CI). Elemental analysis: calculated-C, 45.11; H, 3.44; N, 7.17; found-C, 44.95; H, 3.57; N, 7.16

Step C:

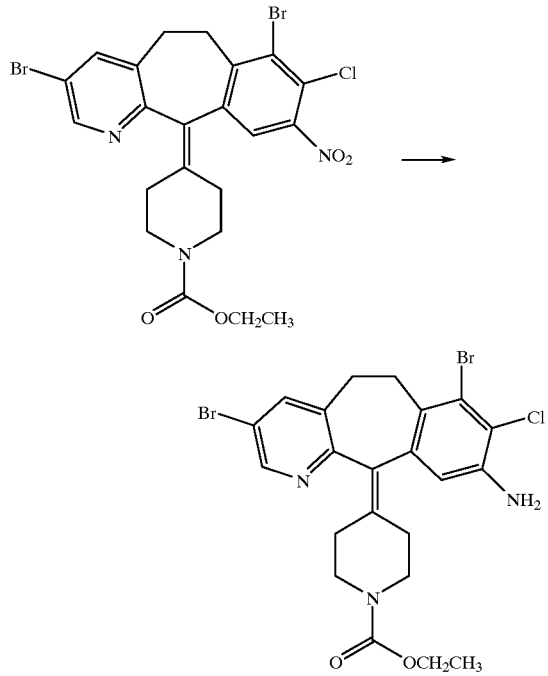

Combine 25 g (447 mmol) of Fe filings, 10 g (90 mmol) of CaCl$_2$ and a suspension of 20 g (34.19 mmol) of the product of Step B in 700 mL of 90:10 EtOH/water at 50° C. Heat the mixture at reflux overnight, filter through Celite® and wash the filter cake with 2×200 mL of hot EtOH. Combine the filtrate and washes, and concentrate in vacuo to a residue. Extract the residue with 600 mL of CH$_2$Cl$_2$, wash with 300 mL of water and dry over MgSO$_4$. Filter and concentrate in vacuo to a residue, then chromatograph (silica gel, 30% EtOAc/CH$_2$Cl$_2$) to give 11.4 g (60% yield) of the product. m.p.=211–212° C., Mass Spec.: MH$^+$=554 (CI). Elemental analysis: calculated-C, 47.55; H, 3.99; N, 7.56; found-C, 47.45; H, 4.31; N, 7.49.

Step D:

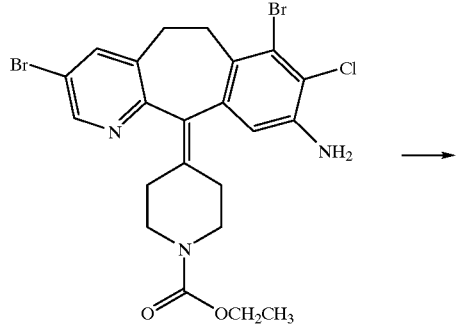

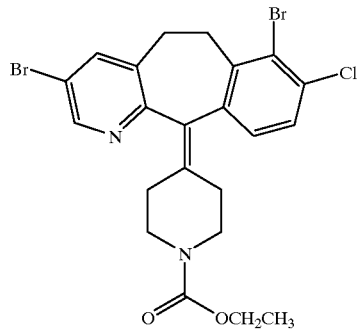

Slowly add (in portions) 20 g (35.9 mmol) of the product of Step C to a solution of 8 g (116 mmol) of NaNO$_2$ in 120 mL of concentrated HCl (aqueous) at −10° C. Stir the resulting mixture at 0° C. for 2 hours, then slowly add (dropwise) 150 mL (1.44 mole) of 50% H$_3$PO$_2$ at 0° C. over a 1 hour period. Stir at 0° C. for 3 hours, then pour into 600 g of ice and basify with concentrated NH$_4$OH (aqueous). Extract with 2×300 mL of CH$_2$Cl$_2$, dry the extracts over MgSO$_4$, then filter and concentrate in vacuo to a residue. Chromatograph the residue (silica gel, 25% EtOAc/hexanes) to give 13.67 g (70% yield) of the product. m.p.=163–165° C., Mass Spec.: MH$^+$=539 (CI). Elemental analysis: calculated-C, 48.97; H, 4.05; N, 5.22; found-C, 48.86; H, 3.91; N, 5.18.

Step E:

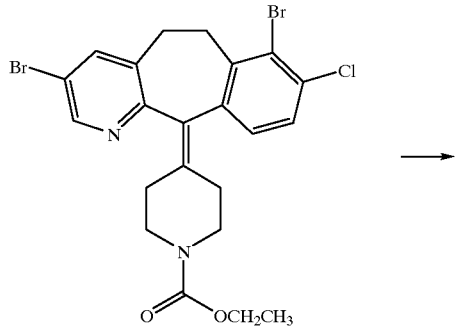

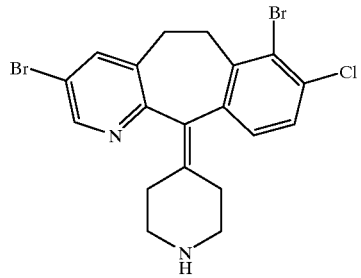

Combine 6.8 g (12.59 mmol) of the product of Step D and 100 mL of concentrated HCl (aqueous) and stir at 85° C. overnight. Cool the mixture, pour it into 300 g of ice and basify with concentrated NH$_4$OH (aqueous). Extract with 2×300 mL of CH$_2$Cl$_2$, then dry the extracts over MgSO$_4$. Filter, concentrate in vacuo to a residue, then chromatograph (silica gel, 10% MeOH/EtOAc+2% NH$_4$OH (aqueous)) to give 5.4 g (92% yield) of the title compound. m.p.= 172–174° C., Mass Spec.: MH+=467 (FAB). Elemental analysis: calculated-C, 48.69; H, 3.65; N, 5.97; found-C, 48.83; H, 3.80; N, 5.97

PREPARATIVE EXAMPLE 3

Step A:

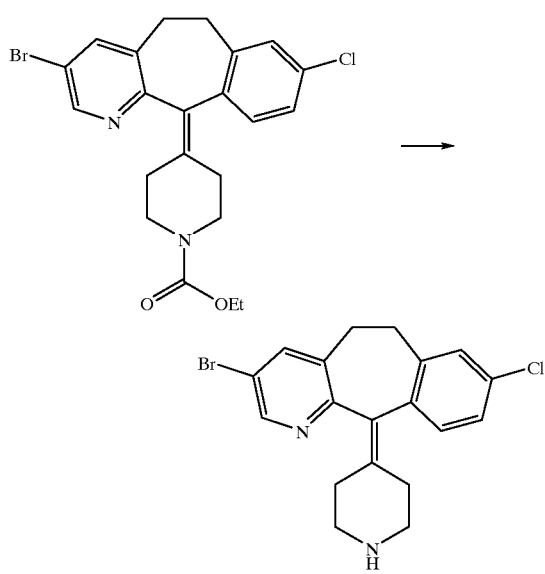

Hydrolyze 2.42 g of 4-(8-chloro-3-bromo-5,6-dihydro-11H-benzo[5,6]cyclohepta[1,2-b]pyridin-11-ylidene)-1-piperidine-1-carboxylic acid ethyl ester via substantially the same procedure as described in Preparative Example 1, Step D, to give 1.39 g (69% yield) of the product.

Step B:

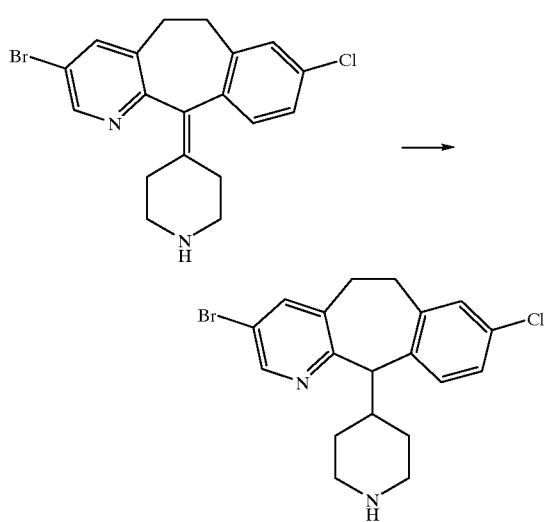

Combine 1 g (2.48 mmol) of the product of Step A and 25 mL of dry toluene, add 2.5 mL of 1 M DIBAL in toluene and heat the mixture at reflux. After 0.5 hours, add another 2.5 mL of 1 M DIBAL in toluene and heat at reflux for 1 hour. (The reaction is monitored by TLC using 50% MeOH/CH$_2$Cl$_2$ +NH$_4$OH (aqueous).) Cool the mixture to room temperature, add 50 mL of 1 N HCl (aqueous) and stir for 5 min. Add 100 mL of 1 N NaOH (aqueous), then extract with EtOAc (3×150 mL). Dry the extracts over MgSO$_4$, filter and concentrate in vacuo to give 1.1 g of the title compound.

PREPARATIVE EXAMPLE 4

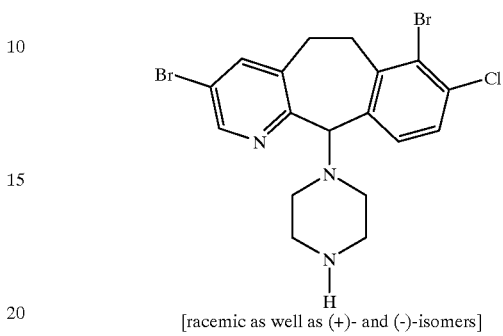

[racemic as well as (+)- and (-)-isomers]

Step A:

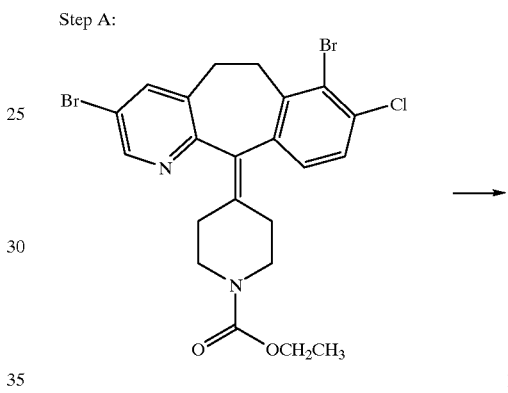

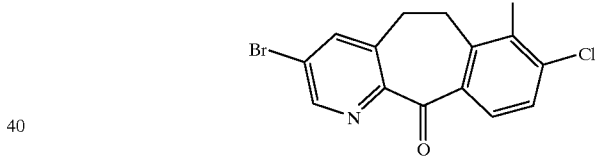

Combine 16.6 g (0.03 mole) of the product of Preparative Example 2, Step D, with a 3:1 solution of CH$_3$CN and water (212.65 mL CH$_3$CN and 70.8 mL of water) and stir the resulting slurry overnight at room temperature. Add 32.833 g (0.153 mole) of NaIO$_4$ and then 0.31 g (2.30 mmol) of RuO$_2$ and stir at room temperature give 1.39 g (69% yield) of the product. (The addition of RuO is accompanied by an exothermic reaction and the temperature climbs from 20° to 30° C.) Stir the mixture for 1.3 hrs. (temperature returned to 25° C. after about 30 min.), then filter to remove the solids and wash the solids with CH$_2$Cl$_2$. Concentrate the filtrate in vacuo to a residue and dissolve the residue in CH$_2$Cl$_2$. Filter to remove insoluble solids and wash the solids with CH$_2$Cl$_2$. Wash the filtrate with water, concentrate to a volume of about 200 mL and wash with bleach, then with water. Extract with 6 N HCl (aqueous). Cool the aqueous extract to 0° C. and slowly add 50% NaOH (aqueous) to adjust to pH=4 while keeping the temperature <30° C. Extract twice with CH$_2$Cl$_2$, dry over MgSO$_4$ and concentrate in vacuo to a residue. Slurry the residue in 20 mL of EtOH and cool to 0° C. Collect the resulting solids by filtration and dry the solids in vacuo to give 7.95 g of the product. $^1$H NMR (CDCl$_3$, 200 MHz): 8.7 (s, 1H); 7.85 (m, 6H); 7.5 (d, 2H); 3.45 (m, 2H); 3.15 (m, 2H).

Step B:

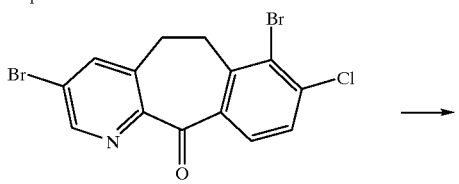

Combine 21.58 g (53.75 mmol) of the product of Step A and 500 mL of an anhydrous 1:1 mixture of EtOH and toluene, add 1.43 g (37.8 mmol) of NaBH$_4$ and heat the mixture at reflux for 10 min. Cool the mixture to 0° C., add 100 mL of water, then adjust to pH≈4~5 with 1 M HCl (aqueous) while keeping the temperature <10° C. Add 250 mL of EtOAc and separate the layers. Wash the organic layer with brine (3×50 mL) then dry over Na$_2$SO$_4$. Concentrate in vacuo to a residue (24.01 g) and chromatograph the residue (silica gel, 30% hexane/CH$_2$Cl$_2$) to give the product. Impure fractions were purified by rechromatography. A total of 18.57 g of the product was obtained. $^1$H NMR (DMSO-d$_6$, 400 MHz): 8.5 (s, 1H); 7.9 (s, 1H); 7.5 (d of d, 2H); 6.2 (s, 1H); 6.1 (s, 1H); 3.5 (m, 1H); 3.4 (m, 1H); 3.2 (m, 2H).

Step C:

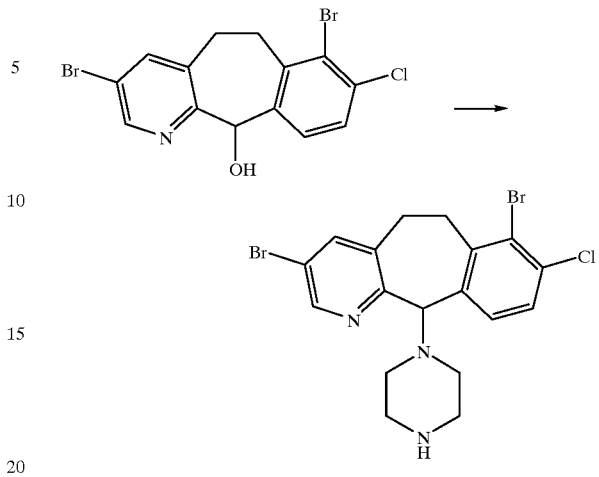

Combine 18.57 g (46.02 mmol) of the product of Step B and 500 mL of CHCl$_3$, then add 6.70 mL (91.2 mmol) of SOCl$_2$, and stir the mixture at room temperature for 4 hrs. Add a solution of 35.6 g (0.413 mole) of piperazine in 800 mL of THF over a period of 5 min. and stir the mixture for 1 hr. at room temperature. Heat the mixture at reflux overnight, then cool to room temperature and dilute the mixture with 1 L of CH$_2$Cl$_2$. Wash with water (5×200 mL), and extract the aqueous wash with CHCl$_3$ (3×100 mL). Combine all of the organic solutions, wash with brine (3×200 mL) and dry over MgSO$_4$. Concentrate in vacuo to a residue and chromatograph (silica gel, gradient of 5%, 7.5%, 10% MeOH/CH$_2$Cl$_2$+NH$_4$OH) to give 18.49 g of the title compound as a racemic mixture.

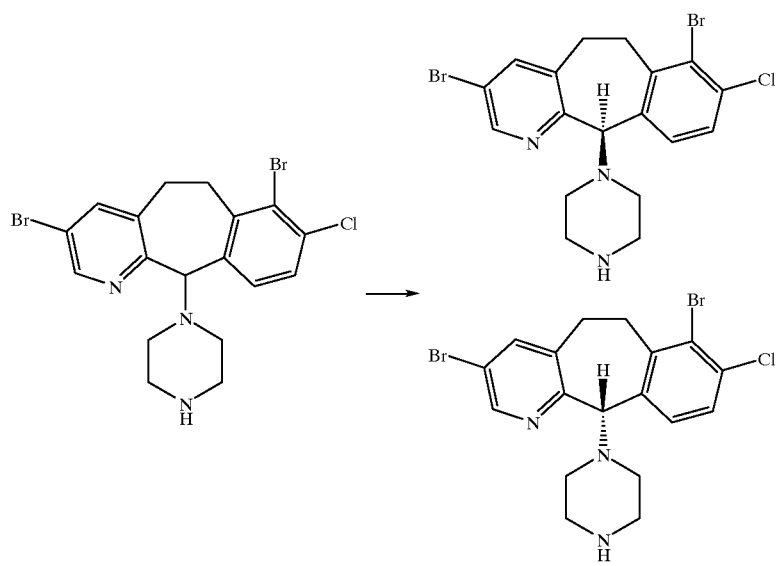

The racemic title compound of Step C is separated by preparative chiral chromatography (Chiralpack AD, 5 cm×50 cm column, flow rate 100 mL/min., 20% iPrOH/hexane+0.2% diethylamine), to give 9.14 g of the (+)-isomer and 9.30 g of the (−)-isomer.

Physical chemical data for (+)-isomer: m.p.=74.5°–77.5° C.; Mass Spec. MH$^+$=471.9; $[\alpha]_D^{25}$=+97.4° (8.48 mg/2 mL MeOH).

Physical chemical data for (−)-isomer: m.p.=82.95–84.5° C.; Mass Spec. MH$^+$=471.8; $[\alpha]_D^{25}$=−97.4° (8.32 mg/2 mL MeOH).

PREPARATIVE EXAMPLE 5

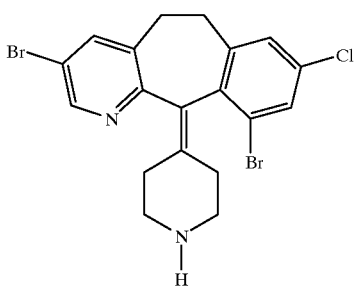

Step A:

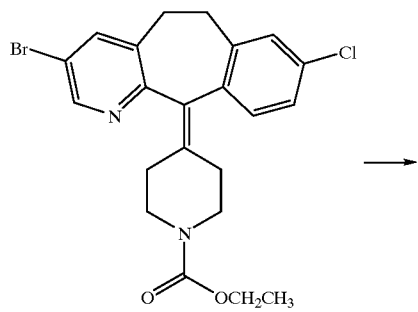

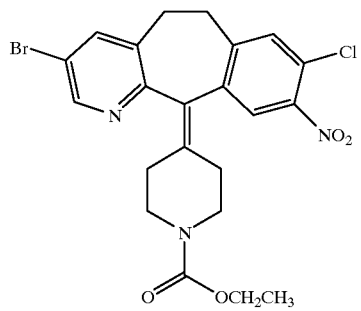

Combine 15 g (38.5 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester and 150 mL of concentrated $H_2SO_4$ at −5° C., then add 3.89 g (38.5 mmol) of $KNO_3$ and stir for 4 hours. Pour the mixture into 3 L of ice and basify with 50% NaOH (aqueous). Extract with $CH_2Cl_2$, dry over $MgSO_4$, then filter and concentrate in vacuo to a residue. Recrystallize the residue from acetone to give 6.69 g of the product. $^1$H NMR (CDCl$_3$, 200 MHz): 8.5 (s, 1H); 7.75 (s, 1H); 7.6 (s, 1H); 7.35 (s, 1H); 4.15 (q, 2H); 3.8 (m, 2H); 3.5–3.1 (m, 4H); 3.0–2.8 (m, 2H); 2.6–2.2 (m, 4H); 1.25 (t, 3H).

Step B:

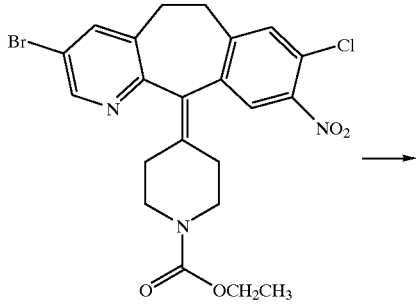

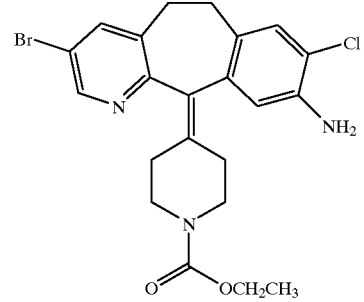

Combine 6.69 g (13.1 mmol) of the product of Step A and 100 mL of 85% EtOH/water, then add 0.66 g (5.9 mmol) of $CaCl_2$ and 6.56 g (117.9 mmol) of Fe and heat the mixture at reflux overnight. Filter the hot reaction mixture through celite® and rinse the filter cake with hot EtOH. Concentrate the filtrate in vacuo to give 7.72 g of the product. Mass Spec.: MH$^+$=478.0

Step C:

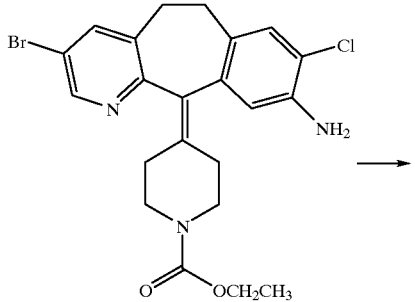

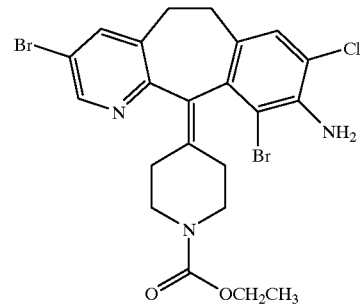

Combine 7.70 g of the product of Step B and 35 mL of HOAc, then add 45 mL of a solution of Br$_2$ in HOAc and stir the mixture at room temperature overnight. Add 300 mL of 1 N NaOH (aqueous), then 75 mL of 50% NaOH (aqueous) and extract with EtOAc. Dry the extract over MgSO$_4$ and concentrate in vacuo to a residue. Chromatograph the residue (silica gel, 20%–30% EtOAc/hexane) to give 3.47 g of the product (along with another 1.28 g of partially purified product). Mass Spec.: MH⁺=555.9.

¹H NMR (CDCl₃, 300 MHz): 8.5 (s, 1H); 7.5 (s, 1H); 7.15 (s, 1H); 4.5 (s, 2H); 4.15 (m, 3H); 3.8 (br s, 2H); 3.4–3.1 (m, 4H); 9–2.75 (m, 1H); 2.7–2.5 (m, 2H); 2.4–2.2 (m, 2H); 1.25 (m, 3H).

Step D:

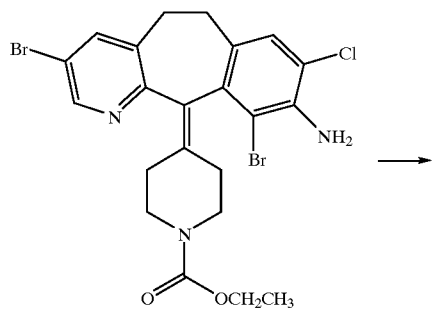

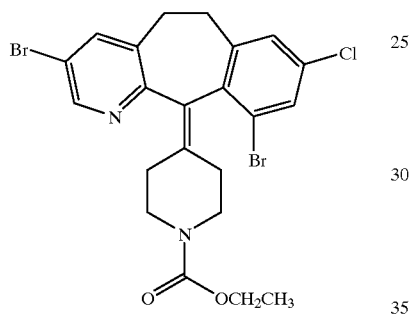

Combine 0.557 g (5.4 mmol) of t-butylnitrite and 3 mL of DMF, and heat the mixture at to 60°–70° C. Slowly add (dropwise) a mixture of 2.00 g (3.6 mmol) of the product of Step C and 4 mL of DMF, then cool the mixture to room temperature. Add another 0.64 mL of t-butylnitrite at 40° C. and reheat the mixture to 60°–70° C. for 0.5 hrs. Cool to room temperature and pour the mixture into 150 mL of water. Extract with CH₂Cl₂, dry the extract over MgSO₄ and concentrate in vacuo to a residue. Chromatograph the residue (silica gel, 10%–20% EtOAc/hexane) to give 0.74 g of the product. Mass Spec.: MH⁺=541.0.

¹H NMR (CDCl3, 200 MHz): 8.52 (s, 1H); 7.5 (d, 2H); 7.2 (s, 1H); 4.15 (q, 2H); 3.9–3.7 (m, 2H); 3.5–3.1 (m, 4H); 3.0–2.5 (m, 2H); 2.4–2.2 (m, 2H); 2.1–1.9 (m, 2H); 1.26 (t, 3H).

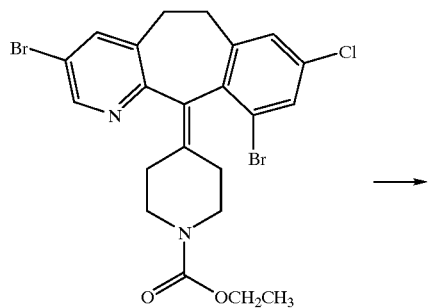

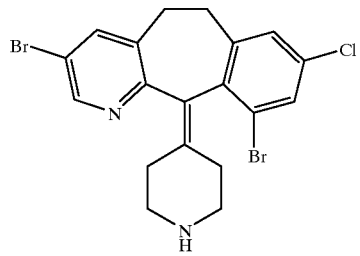

Combine 0.70 g (1.4 mmol) of the product of Step D and 8 mL of concentrated HCl (aqueous) and heat the mixture at reflux overnight. Add 30 mL of 1 N NaOH (aqueous), then 5 mL of 50% NaOH (aqueous) and extract with CH₂Cl₂. Dry the extract over MgSO₄ and concentrate in vacuo to give 0.59 g of the title compound. Mass Spec.: M⁺=468.7. m.p.=123.9°–124.2° C.

PREPARATIVE EXAMPLE 6

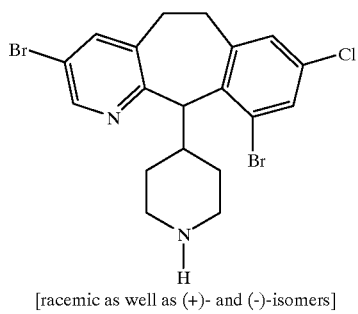

[racemic as well as (+)- and (-)-isomers]

Step A:

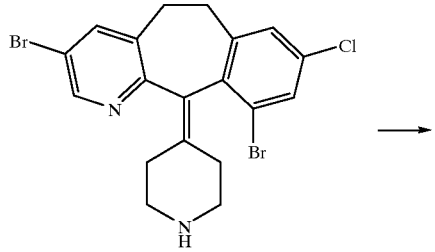

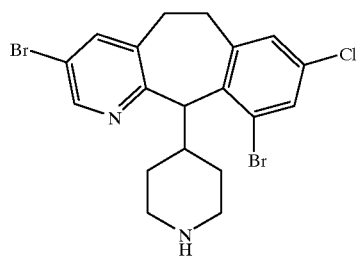

Prepare a solution of 8.1 g of the title compound from Preparative Example 5, Step E, in toluene and add 17.3 mL of a 1M solution of DIBAL in toluene. Heat the mixture at reflux and slowly add (dropwise) another 21 mL of 1 M DIBAL/toluene solution over a period of 40 min. Cool the reaction mixture to about 0° C. and add 700 mL of 1 M HCl (aqueous). Separate and discard the organic phase. Wash the aqueous phase with CH₂Cl₂, discard the extract, then basify the aqueous phase by adding 50% NaOH (aqueous). Extract with CH₂Cl₂, dry the extract over MgSO₄ and concentrate in vacuo to give 7.30 g of the title compound, which is a racemic mixture of enantiomers.

Step B-Separation of Enantiomers:

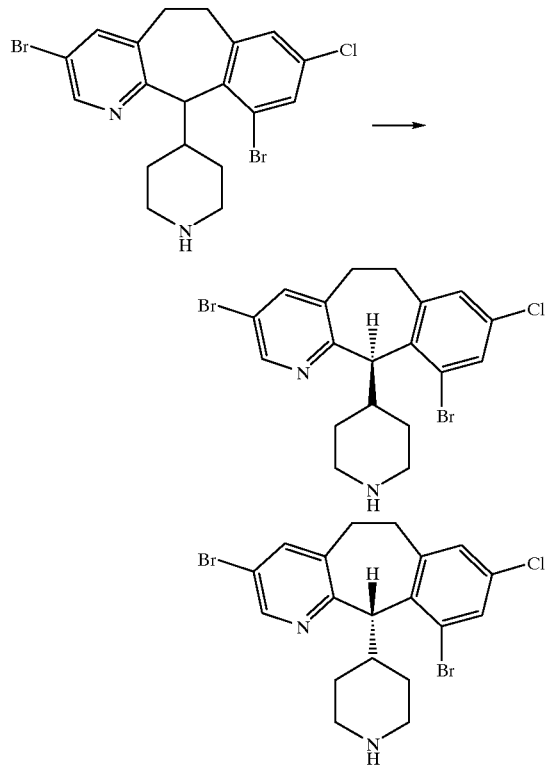

The racemic title compound of Step A is separated by preparative chiral chromatography (Chiralpack AD, 5 cm×50 cm column, using 20% iPrOH/hexane+0.2% diethylamine), to give the (+)-isomer and the (−)-isomer of the title compound.

Physical chemical data for (+)-isomer: m.p.=148.8° C.; Mass Spec. MH$^+$=469; $[\alpha]_D^{25}$=+65.6° (12.93 mg/2 mL MeOH).

Physical chemical data for (−)-isomer: m.p.=112° C.; Mass Spec. MH$^+$=469; $[\alpha]_D^{25}$=−65.2° (3.65 mg/2 mL MeOH).

PREPARATIVE EXAMPLE 7

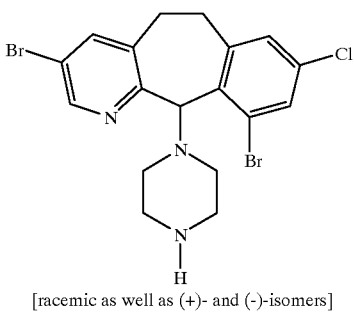

[racemic as well as (+)- and (−)-isomers]

-continued

Step A:

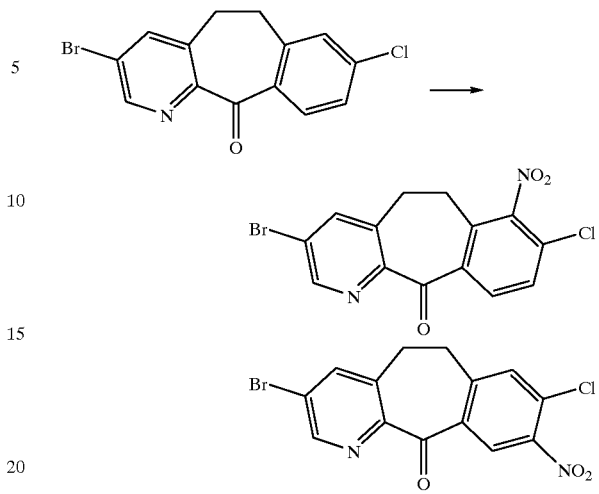

Combine 40.0 g (0.124 mole) of the starting ketone and 200 mL of H$_2$SO$_4$ and cool to 0° C. Slowly add 13.78 g (0.136 mole) of KNO$_3$ over a period of 1.5 hrs., then warm to room temperature and stir overnight. Work up the reaction using substantially the same procedure as described for Preparative Example 2, Step A. Chromatograph (silica gel, 20%, 30%, 40%, 50% EtOAc/hexane, then 100% EtOAc) to give 28 g of the 9-nitro product, along with a smaller quantity of the 7-nitro product and 19 g of a mixture of the 7-nitro and 9-nitro compounds.

Step B:

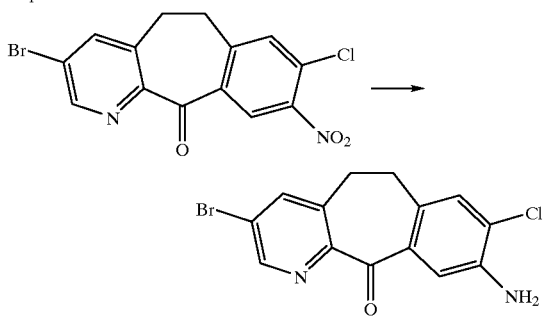

React 28 g (76.2 mmol) of the 9-nitro product of Step A, 400 mL of 85% EtOH/water, 3.8 g (34.3 mmol) of CaCl$_2$ and 38.28 g (0.685 mole) of Fe using substantially the same procedure as described for Preparative Example 2, Step C, to give 24 g of the product Step C:

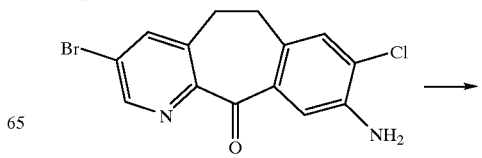

-continued

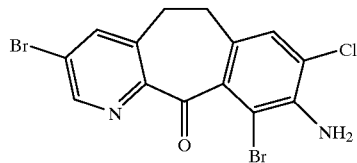

Combine 13 g (38.5 mmol) of the product of Step B, 140 mL of HOAc and slowly add a solution of 2.95 mL (57.8 mmol) of $Br_2$ in 10 mL of HOAc over a period of 20 min. Stir the reaction mixture at room temperature, then concentrate in vacuo to a residue. Add $CH_2Cl_2$ and water, then adjust to pH=8–9 with 50% NaOH (aqueous). Wash the organic phase with water, then brine and dry over $Na_2SO_4$. Concentrate in vacuo to give 11.3 g of the product.

Step D:

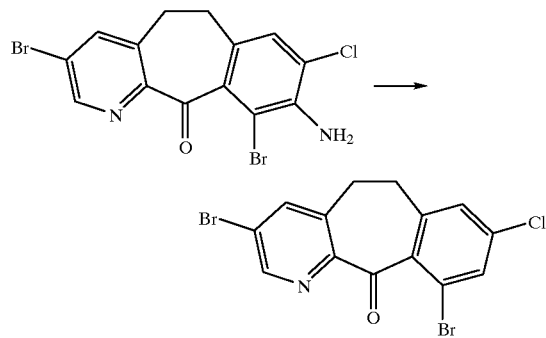

Cool 100 mL of concentrated HCl (aqueous) to 0° C., then add 5.61 g (81.4 mmol) of $NaNO_2$ and stir for 10 min. Slowly add (in portions) 11.3 g (27.1 mmol) of the product of Step C and stir the mixture at 0°–3° C. for 2.25 hrs. Slowly add (dropwise) 180 mL of 50% $H_3PO_2$ (aqueous) and allow the mixture to stand at 0° C. overnight. Slowly add (dropwise) 150 mL of 50% NaOH over 30 min., to adjust to pH=9, then extract with $CH_2Cl_2$. Wash the extract with water, then brine and dry over $Na_2SO_4$. Concentrate in vacuo to a residue and chromatograph (silica gel, 2% EtOAc/$CH_2Cl_2$) to give 8.6 g of the product.

Step E:

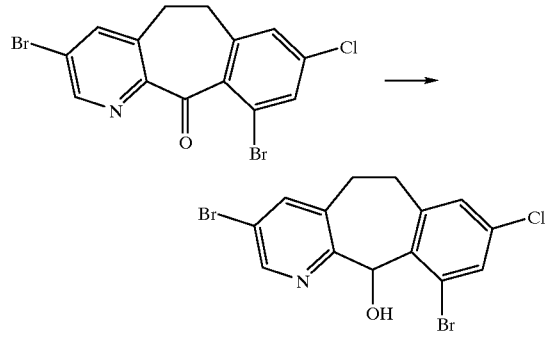

Combine 8.6 g (21.4 mmol) of the product of Step D and 300 mL of MeOH and cool to 0°–2° C. Add 1.21 g (32.1 mmol) of $NaBH_4$ and stir the mixture at ~0° C. for 1 hr. Add another 0.121 g (3.21 mmol) of $NaBH_4$, stir for 2 hr. at 0° C., then let stand overnight at 0° C. Concentrate in vacuo to a residue then partition the residue between $CH_2Cl_2$ and water. Separate the organic phase and concentrate in vacuo (50° C.) to give 8.2 g of the product.

Step F:

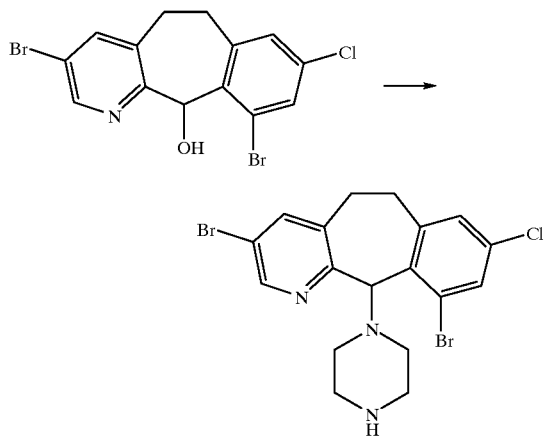

Combine 8.2 g (20.3 mmol) of the product of Step E and 160 mL of $CH_2Cl_2$, cool to 0° C., then slowly add (dropwise) 14.8 mL (203 mmol) of $SOCl_2$ over a 30 min. period. Warm the mixture to room temperature and stir for 4.5 hrs., then concentrate in vacuo to a residue, add $CH_2Cl_2$ and wash with 1 N NaOH (aqueous) then brine and dry over $Na_2SO_4$. Concentrate in vacuo to a residue, then add dry THF and 8.7 g (101 mmol) of piperazine and stir at room temperature overnight. Concentrate in vacuo to a residue, add $CH_2Cl_2$, and wash with 0.25 N NaOH (aqueous), water, then brine. Dry over $Na_2SO_4$ and concentrate in vacuo to give 9.46 g of the crude product. Chromatograph (silica gel, 5% MeOH/$CH_2Cl_2$+$NH_3$) to give 3.59 g of the title compound, as a racemate. $^1$H NMR ($CDCl_3$, 200 MHz): 8.43 (d, 1H); 7.55 (d, 1H); 7.45 (d, 1H); 7.11 (d, 1H); 5.31 (s, 1H); 4.86–4.65 (m, 1H); 3.57–3.40 (m, 1H); 2.98–2.55 (m, 6H); 2.45–2.20 (m, 5H).

Step G - Separation of Enantiomers:

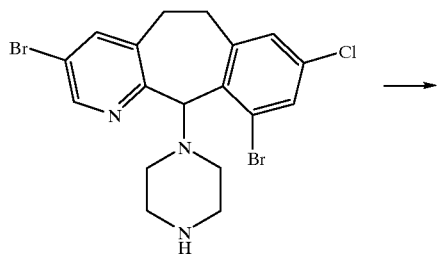

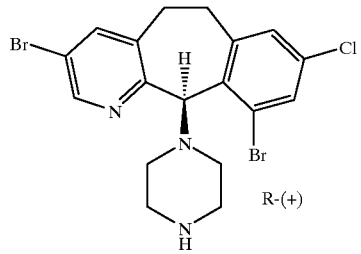

R-(+)

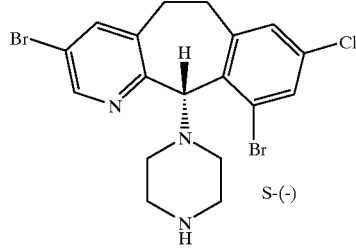

S-(-)

The racemic title compound from Step F (5.7 g) is chromatographed as described for Preparative Example 4, Step D, using 30% iprOH/hexane+0.2% diethylamine, to give 2.88 g of the R-(+)-isomer and 2.77 g of the S-(-)-isomer of the title compound.

Physical chemical data for the R-(+)-isomer: Mass Spec. MH$^+$=470.0; $[\alpha]_D^{25}$=+12.1° (10.9 mg/2 mL MeOH).

Physical chemical data for the S-(-)-isomer: Mass Spec. MH$^+$=470.0; $[\alpha]_D^{25}$=-13.2° (11.51 mg/2 mL MeOH).

PREPARATIVE EXAMPLE 8

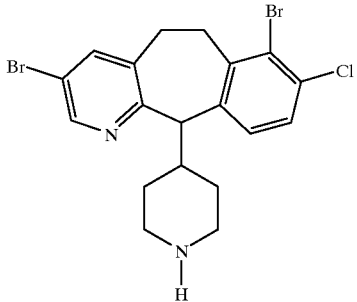

[racemic as well as (+)- and (-)-isomers]

Step A:

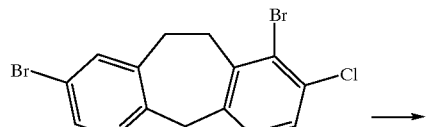

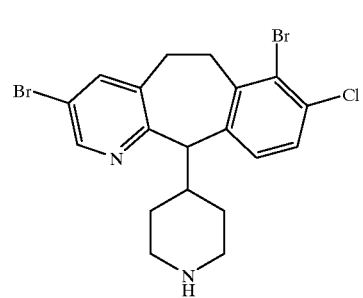

Combine 13 g (33.3 mmol) of the title compound from Preparative Example 2, Step E, and 300 mL of toluene at 20° C., then add 32.5 mL (32.5 mmol) of a 1 M solution of DIBAL in toluene. Heat the mixture at reflux for 1 hr., cool to 20° C., add another 32.5 mL of 1 M DIBAL solution and heat at reflux for 1 hr. Cool the mixture to 20° C. and pour it into a mixture of 400 g of ice, 500 mL of EtOAc and 300 mL of 10% NaOH (aqueous). Extract the aqueous layer with CH$_2$Cl$_2$ (3×200 mL), dry the organic layers over MgSO$_4$, then concentrate in vacuo to a residue. Chromatograph (silica gel, 12% MeOH/CH$_2$Cl$_2$+4% NH$_4$OH) to give 10.4 g of the title compound as a racemate. Mass Spec.: MH$^+$=469 (FAB). Partial $^1$H NMR (CDCl$_3$, 400 MHz): 8.38 (s, 1H); 7.57 (s, 1H); 7.27 (d, 1H); 7.06 (d, 1H); 3.95 (d, 1H).

Step B - Separation of Enantiomers:

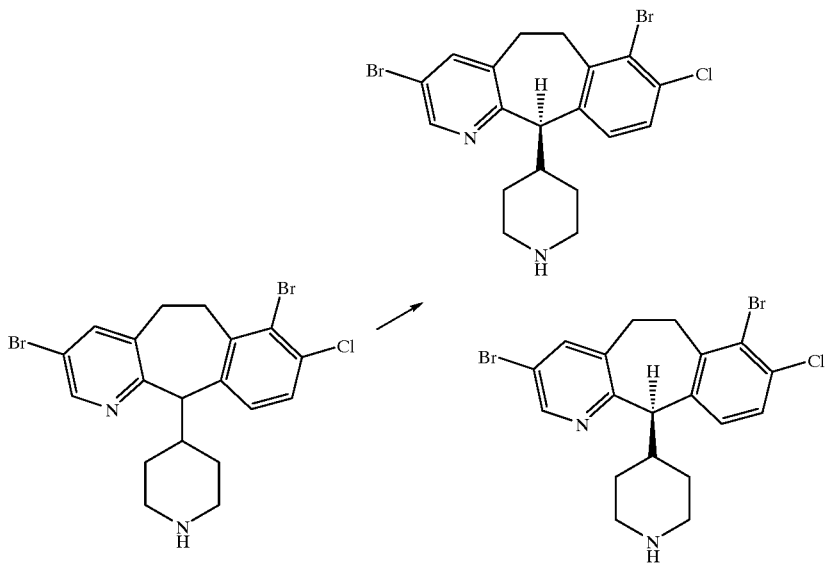

The racemic title compound of Step A is separated by preparative chiral chromatography (Chiralpack AD, 5 cm×50 cm column, using 5% iPrOH/hexane+0.2% diethylamine), to give the (+)-isomer and the (−)-isomer of the title compound.

Physical chemical data for (+)-isomer: Mass Spec. MH$^+$= 469 (FAB); $[\alpha]_D^{25}$=+43.5° (c=0.402, EtOH); partial $^1$H NMR (CDCl$_3$, 400 MHz): 8.38 (s, 1H); 7.57 (s, 1H); 7.27 (d, 1H); 7.05 (d, 1H); 3.95 (d, 1H).

Physical chemical data for (−)-isomer: Mass Spec. MH$^+$= 469 (FAB); $[\alpha]_D^{25}$=−41.8° (c=0.328 EtOH); partial $^1$H NMR (CDCl$_3$, 400 MHz): 8.38 (s, 1H); 7.57 (s, 1H); 7.27 (d, 1H); 7.05 (d, 1H); 3.95 (d, 1H).

PREPARATIVE EXAMPLE 9

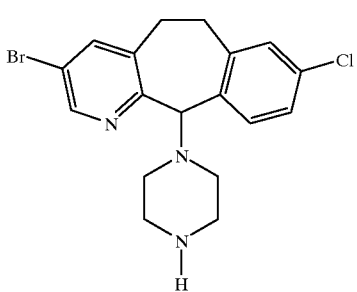

[racemic as well as R-(+)- and S-(−)-isomers]

The compound

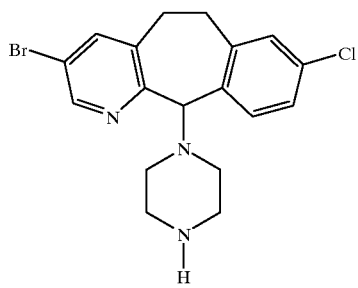

is prepared according to the procedures of Preparative Example 40 of WO 95/10516 (published Apr. 20, 1995), by following the procedures described in Example 193 of WO 95/10516.

The (+)- and (−)-isomers can be separated by following essentially the same procedure as Step D of Preparative Example 4.

Physical chemical data for the R-(+)-isomer: $^{13}$C NMR (CDCl$_3$): 155.8 (C); 146.4 (CH); 140.5 (CH); 140.2 (C); 136.2 (C); 135.3 (C); 133.4 (C); 132.0 (CH); 129.9 (CH); 125.6 (CH); 119.3 (C); 79.1 (CH); 52.3 (CH$_2$); 52.3 (CH); 45.6 (CH$_2$); 45.6 (CH$_2$); 30.0 (CH$_2$); 29.8 (CH$_2$). $[\alpha]_D^{25}$=+25.8° (8.46 mg/2 mL MeOH).

Physical chemical data for the S-(−)-isomer: $^{13}$C NMR (CDCl$_3$): 155.9 (C); 146.4 (CH); 140.5 (CH); 140.2 (C); 136.2 (C); 135.3 (C); 133.3 (C); 132.0 (CH); 129.9 (CH); 125.5 (CH); 119.2 (C); 79.1 (CH); 52.5 (CH$_2$); 52.5 (CH); 45.7 (CH$_2$); 45.7 (CH$_2$); 30.0 (CH$_2$); 29.8 (CH$_2$). $[\alpha]_D^{25}$=−27.9° (8.90 mg/2 mL MeOH).

PREPARATIVE EXAMPLE 10

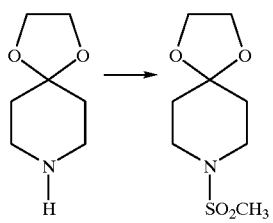

To a solution of 1,4-dioxa-8-azaspiro(4,5)decane (14.3 mL, 0.112 mol) dissolved in anhydrous dichloromethane (300 mL) was added triethylamine (23.5 mL, 0.168 mol) and methanesulfonyl chloride (8.68 mL, 0.112 mol) at 0° C. The reaction mixture was warmed to room temperature and stirred overnight. Aqueous $NaH_2PO_4$ (10%) was added to the mixture and stirred for 1 hour. The phases were separated and the aqueous phase was extracted with dichloromethane. The combined organic phases were washed with brine, dried over anhydrous $MgSO_4$, filtered and concentrated in vacuo to afford 1,4-dioxa-8-(methylsulfonyl)azaspiro-(4,5)decane (22.9 g, 92%).

PREPARATIVE EXAMPLE 11

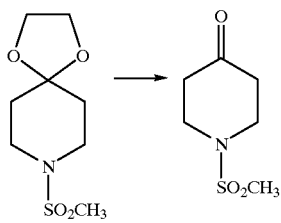

A mixture of the compound from Preparative Example 10 (22.9 g, 0.103 mol), tetrahydrofuran-water (1:1 v/v, 600 mL) and oxalic acid (228 g, 2.53 mol) was refluxed for 1 hour. Acetic acid (60 mL, 1.048 mol) was added and the resulting mixture was refluxed for an additional 3 hours. The reaction mixture was concentrated in vacuo, diluted with dichloromethane and washed with aqueous sodium bicarbonate (saturated solution). The organic phase was washed with brine, dried over anhydrous $MgSO_4$, filtered and concentrated in vacuo to afford 4-[1-(methylsulfonyl)]piperidone [14.04 g, 77%, FAB-MS 178 ($MH^+$, 100% )].

PREPARATIVE EXAMPLE 12

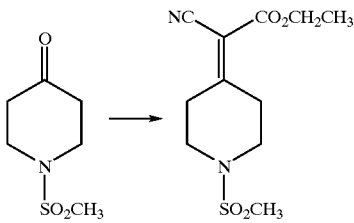

A mixture of the title compound from Preparative Example 11 (12.9 g, 73 mmol), ethyl cyanoacetate (11.7 mL, 0.11 mol), ammonium acetate (0.88 g, 14.7 mmol), acetic acid (3.4 mL, 59 mmol) and benzene (250 mL) was refluxed in a round-bottom flask attached with a Dean-Stark trap overnight. The reaction mixture was cooled to room temperature, concentrated in vacuo, diluted with dichloromethane and washed with saturated aqueous sodium bicarbonate solution. The organic phase was dried over anhydrous $MgSO_4$, filtered and concentrated in vacuo to afford a solid which was combined with diethylether (200 mL) and filtered to provide ethyl 4-[1-(methylsulfonyl)piperidinylidenyl]cyanoacetate [16 g, 81%, FAB-MS 273 ($MH^+$, 100%)].

PREPARATIVE EXAMPLE 13

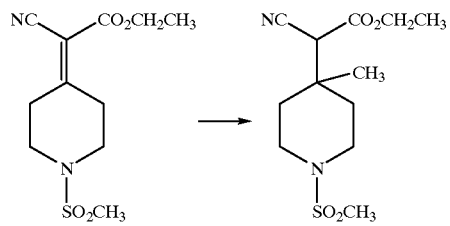

To a mixture of Cu(I)Cl (350 mg) in anhydrous tetrahydrofuran (2 mL) at 0° C. was added dropwise methylmagnesium iodide (2.5 mL of 3.0 M solution in diethylether). The title compound from Preparative Example 12 dissolved in tetrahydrofuran (THF, 150 mL) was added via cannula over 1 hour. The ice-water bath was removed and the mixture was stirred at room temperature for 2 hours. The reaction mixture was poured into a mixture of 10% sulfuric acid (50 mL) and ice (50 g), then extracted with cichloromethane. The organic phase was dried over anhydrous $MgSO_4$, filtered and concentrated in vacuo to afford ethyl 4-[4-methyl-1-(methylsulfonyl)-piperidinyl]cyanoacetate [1.49 g, 100%, FAB-MS 289 ($MH^+$, 100%)].

PREPARATIVE EXAMPLE 14

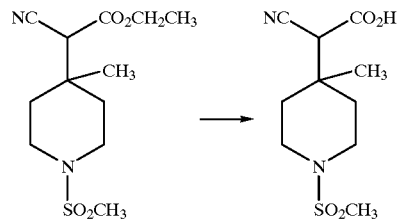

A mixture of the title compound from Preparative Example 13 (3.06 g, 10.6 mmol) and 10% aqueous sodium hydroxide (10 mL) was stirred at room temperature under nitrogen overnight. The reaction mixture was washed with diethylether, dichloromethane, and ethyl acetate and the aqueous phase was acidified with 10% hydrochloric acid to a pH of 1.0. The volume of water was reduced in vacuo, brine was added and the remaining mixture was extracted with dichloromethane. The organic phase was dried over anhydrous $MgSO_4$, filtered and concentrated in vacuo to afforded 4-[4-methyl-1-(methylsulfonyl)-piperidinyl]cyanoacetic acid [0.80 g, 29%, FAB-MS 261 ($MH^+$,38%), 283 (M+ $Na^+$,100%)].

PREPARATIVE EXAMPLE 15

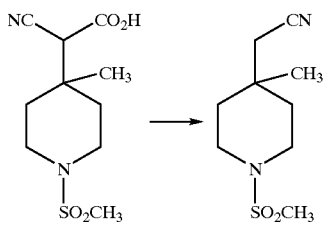

The title compound from Preparative Example 14 (0.60 g, 2.3 mmol) dissolved in anhydrous N,N-dimethylformamide (20 mL) was stirred at 130° C. overnight. Concentration in vacuo afforded 4-cyanomethyl-4-methyl-1-(methylsulfonyl)- piperidine which was used directly in Preparative Example 16 [FAB-MS 289 (MH+, 100%)].

PREPARATIVE EXAMPLE 16

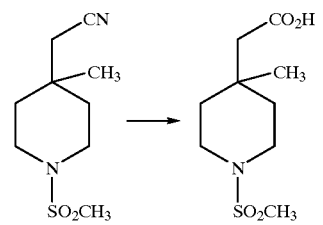

A mixture of the title compound from Preparative Example 15 and concentrated hydrochloric acid (10 mL) was stirred at reflux for 3 days. The reaction mixture was concentrated in vacuo, diluted with dichloromethane and washed with saturated aqueous sodium bicarbonate. The organic phase was dried over anhydrous MgSO$_4$, filtered and concentrated in vacuo to afford 4-[4-methyl-1-(methylsulfonyl)-piperidinyl]acetic acid (90 mg, 17%, FAB-MS 236 (MH+, 100%)].).

PREPARATIVE EXAMPLE 17

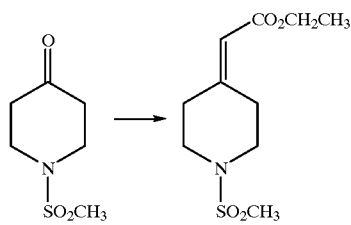

To a cooled (−78° C.) solution of lithium diisopropylamide (0.5 mL, 1 mmol) in 0.5 mL THF was added tert-butyltrimethylsilyl acetate (0.22 mL, 1 mmol). After stirring for 10 min, the title compound from Preparative Example 11 (0.18 g, 1 mmol) dissolved in THF (1 mL) was added dropwise and the reaction mixture was allowed to warm to room temperature and stir for several hours. The reaction was quenched with 10% hydrochloric acid, extracted with dichloromethane, dried over anhydrous MgSO$_4$, filtered and concentrated in vacuo. The residue was purified by prep plate chromatography (silica) using 25% ethyl acetate-hexane to give ethyl 4-[1-(methylsulfonyl) piperidinylidenyl]acetate [0.14 g, 50%, CI-MS 276 (MH+)].

PREPARATIVE EXAMPLE 18

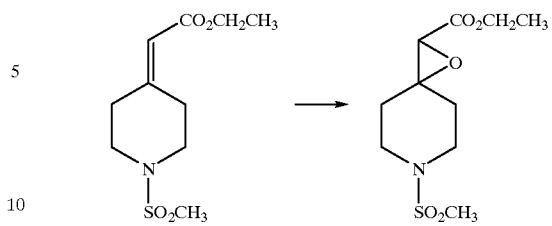

Dissolve the title compound from Preparative Example 17 (1 mmol) in methanol (10 mL) and to it add 30% hydrogen peroxide (3 mmol) and aqueous sodium hydroxide (1.5 mmol). Stir the reaction mixture at room temperature over night. Dilute the reaction with dichloromethane, wash with brine, dry over anhydrous MgSO$_4$, filter and concentrate in vacuo to give ethyl 4-[1-(methylsulfonyl)piperidinylidenyl]-α,β-epoxyacetate.

PREPARATIVE EXAMPLE 19

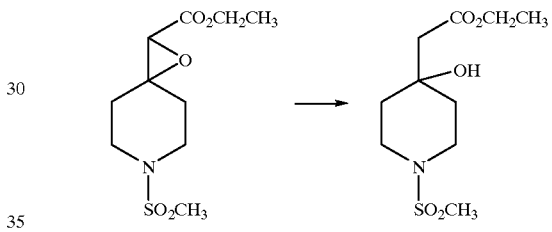

Dissolve the title compound from Preparative Example 18 (1 mmol) in methanol (10 mL), combine with 10% Palladium on carbon and shake in a Parr hydrogenator under hydrogen gas atmosphere. Filter and concentrate of the filtrate to afford ethyl 4-hydroxy-4-[1-(methylsulfonyl) piperidinylidenyl]acetate.

PREPARATIVE EXAMPLE 20

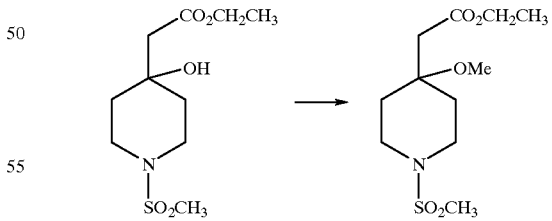

Dissolve the title compound from Preparative Example 19 (1 mmol) in DMF (10 mL) and to this solution add sodium hydride (1 mmol). After gas evolution ceases, add methyl iodide and stir the reaction mixture at room temperature for several hours. Concentrate in vacuo, dilute with dichloromethane and wash with water to give ethyl 4-hydroxy-4-[1-(methylsulfonyl)-piperidinylidenyl]acetate.

PREPARATIVE EXAMPLE 21

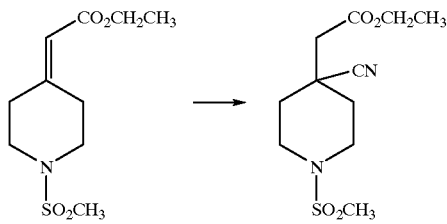

Stir the title compound from Preparative Example 17 (1 mmol) in DMSO (10 mL) with sodium cyanide (1 mmol) and heat at 50° C. for several days. Cool to room temperature, pour into water, acidify to pH 4 with glacial acetic acid, and extract with dichloromethane. Concentrate in vacuo, dry over anhydrous $MgSO_4$, filter and concentrate in vacuo to give ethyl 4-cyano-4-[1-)methylsulfonyl)-piperidinylidenyl]acetate.

PREPARATIVE EXAMPLE 22

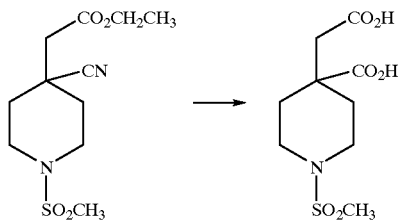

Stir the title compound from Preparative Example 21 (1 mmol) in 3M aqueous potassium hydroxide (5 mmol) at 50–100° C. for several days. Cool to room temperature, acidify to pH 4 with 1M HCl, and concentrate in vacuo to give 4-carboxy-4-[1-(methylsulfonyl)piperidinylidenyl] acetic acid.

PREPARATIVE EXAMPLE 23

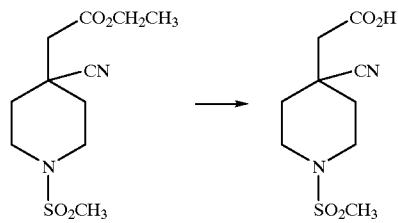

Stir the title compound from Preparative Example 21 (1 mmol) in aqueous lithium hydroxide (1 mmol) at 25° C. for several hours. Cool to room temperature, acidify to pH 4 with 1M HCl, and concentrate in vacuo to give 4-cyano-4-[1-(methylsulfonyl)piperidinylidenyl]acetic acid.

EXAMPLE 1

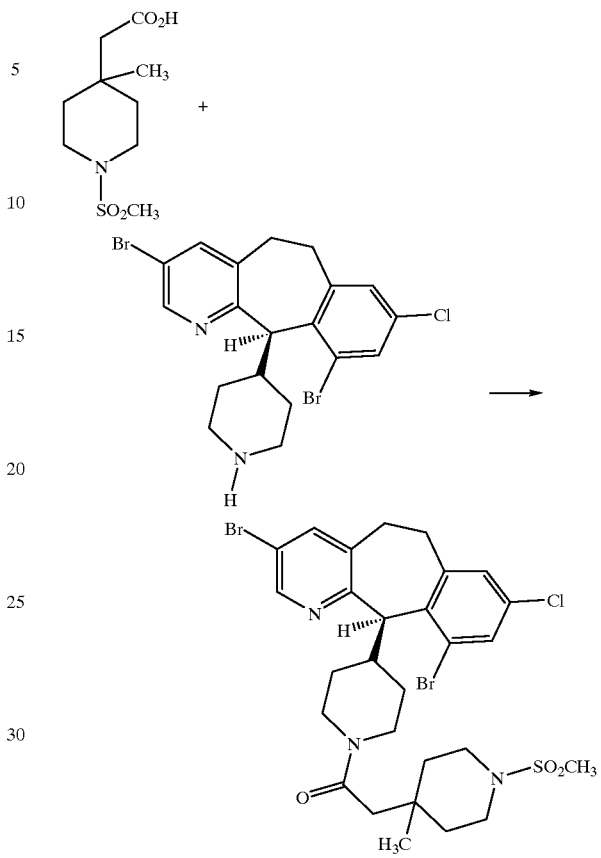

To the title compound from Preparative Example 16 (90 mg, 0.38 mmol) dissolved in anhydrous N,N-dimethylformamide (DMF, 3 mL) was added 1-hydroxybenzotriazole hydrate (52 mg, 0.38 mmol), 1-(3-dimethylaminopropyl)-3-ethylcarbodiimide hydrochloride (73 mg, 0.38 mmol), (+)-3,10-dibromo-8-chloro-6,11-dihydro-11-(4-piperidinyl)-5H-benzo[5,6]cyclohepta[1,2-b] pyridine from Preparative Example 6 (100 mg, 0.21 mmol) and N-methylmorpholine (0.042 mL, 0.38 mmol) and the resulting mixture was stirred at room temperature under nitrogen overnight. Concentration in vacuo provided a residue which was diluted with dichloromethane, washed with 1M hydrochloric acid and 1 M aqueous sodium hydroxide and brine, then dried over anhydrous magnesium sulfate. Filtration and concentration in vacuo afforded (+)-4-(3,10-dibromo-8-chloro-6,11-dihydro-5H-benzo[5,6]cyclohepta[1,2-b]pyridin-11(R)-yl)-1-[[4-methyl-1-(methylsulfonyl)-4-pyridinyl]acetyl]piperidine [43 mg, 30%, mp=105–109° C.; FAB-MS 688 ($MH^+$, 100%)].

EXAMPLE 2

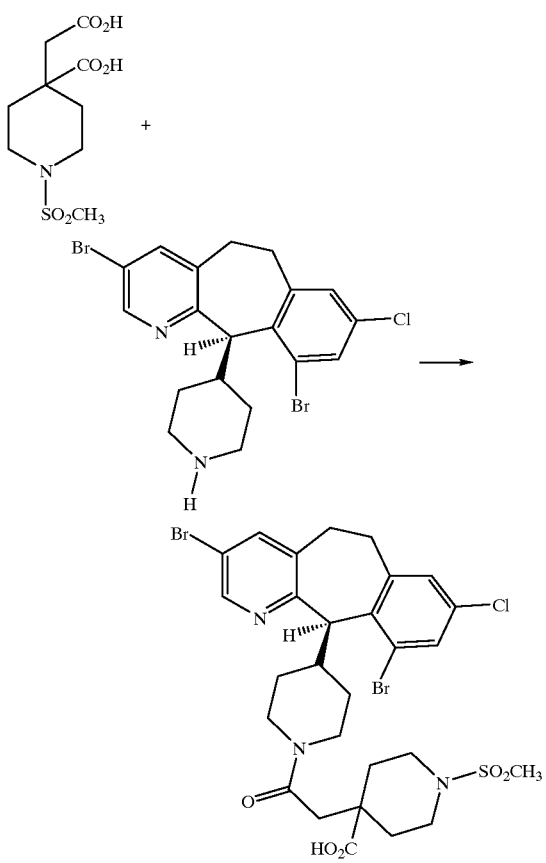

Dissolve the title compound from Preparative Example 22 (1 mmol) in anhydrous N,N-dimethylformamide (DMF, 10 mL) and add 1-hydroxybenzotriazole hydrate (1 mmol), 1-(3-dimethylaminopropyl)-3-ethylcarbodiimide hydrochloride (1 mmol), (+)-3,10-dibromo-8-chloro-6,11-dihydro-11-(4-piperidinyl)-5H-benzo[5,6]cyclohepta[1,2-b]pyridine from Preparative Example 6 (1 mmol) and N-methylmorpholine (1 mmol). Stir the resulting mixture at room temperature under nitrogen overnight. Concentrate in vacuo to provide a residue and dilute with dichloromethane, wash with 1M hydrochloric acid and brine, then dry over anhydrous magnesium sulfate. Filter and concentrate in vacuo to afford (+) -4-(3,10-dibromo-8-chloro-6,11-dihydro-5H-benzo[5,6]cyclohepta[1,2-b]pyridin-11(R)-yl)-1-[[4-carboxy-1-(methylsulfonyl)-4-pyridinyl]acetyl]piperidine.

EXAMPLE 3

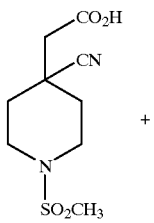

+

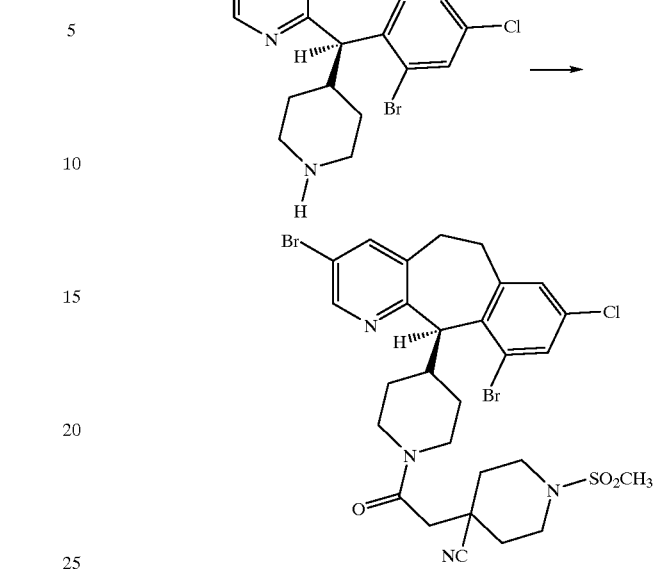

Dissolve the title compound from Preparative Example 23 (1 mmol) in anhydrous N,N-dimethylformamide (DMF, 10 mL) and add 1-hydroxybenzotriazole hydrate (1 mmol), 1-(3-dimethylaminopropyl)-3-ethylcarbodiimide hydrochloride (1 mmol), (+)-3,10-dibromo-8-chloro-6,11-dihydro-11-(4-piperidinyl)-5H-benzo[5,6]cyclohepta[1,2-b]pyridine from Preparative Example 6 (1 mmol). Stir the resulting mixture at room temperature under nitrogen overnight. Concentrate in vacuo to provide a residue and dilute with dichloromethane, wash with 1M hydrochloric acid and brine, then dry over anhydrous magnesium sulfate. Filter and concentrate in vacuo affords (+)-4-(3,10-dibromo-8-chloro-6,11-dihydro-5H-benzo[5,6]cyclohepta[1,2-b]pyridin-11(R)-yl)-1-[[4-cyano-1-(methylsulfonyl)-4-pyridinyl]acetyl]piperidine.

EXAMPLE 4

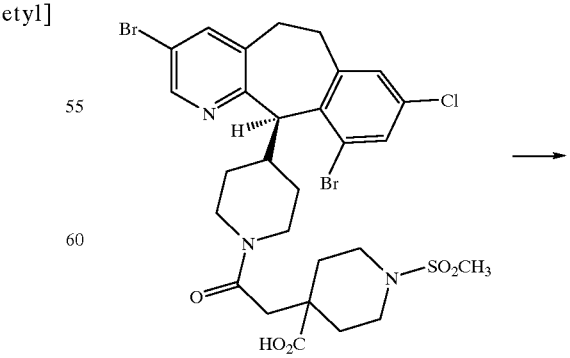

-continued

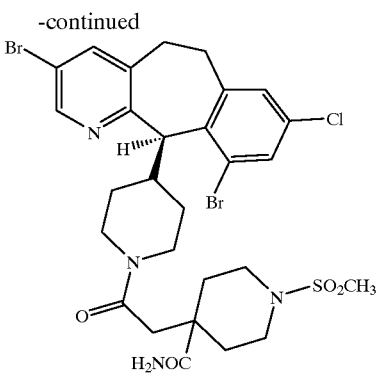

Dissolve the title compound from Example 2 (1 mmol) in anhydrous N,N-dimethylformamide (DMF, 10 mL) and add 1-hydroxybenzotriazole hydrate (1 mmol), 1-(3-dimethylaminopropyl)-3-ethylcarbodiimide hydrochloride (1 mmol), ammonium chloride (1 mmol) and N-methylmorpholine (1 mmol). Stir the resulting mixture at room temperature under nitrogen overnight. Concentrate in vacuo to provide a residue and dilute with dichloromethane, wash with 1M hydrochloric acid and brine, then dry over anhydrous magnesium sulfate. Filter and concentrate in vacuo to afford (+)-4-(3,10-dibromo-8-chloro-6,11-dihydro-5H-benzo[5,6]cyclohepta[1,2-b]pyridin-11(R)-yl)-1-[[4-cyano-1-(methylsulfonyl)-4-pyridinyl]acetyl]piperidine.

Assays

FPT $IC_{50}$ (inhibition of farnesyl protein transferase, in vitro enzyme assay) and COS Cell $IC_{50}$ (Cell-Based Assay) were determined following the assay procedures described in WO 95/10516, published Apr. 20, 1995. GGPT $IC_{50}$ (inhibition of geranylgeranyl protein transferase, in vitro enzyme assay), Cell Mat Assay, and anti-tumor activity (in vivo anti-tumor studies) could be determined by the assay procedures described in WO 95/10516. The disclosure of WO 95/10516 is incorporated herein by reference thereto. The compound of Example 1 above demonstrated a FPT $IC_{50}$ of 19 nM and a COS Cell $IC_{50}$ of 22 nM.

Additional assays can be carried out by following essentially the same procedure as described above, but with substitution of alternative indicator tumor cell lines in place of the T24-BAG cells. The assays can be conducted using either DLD-1-BAG human colon-carcinoma cells expressing an activated K-ras gene or SW620-BAG human colon carcinoma cells expressing an activated K-ras gene. Using other tumor cell lines known in the art, the activity of the compounds of this invention against other types of cancer cells could be demonstrated.

Soft Agar Assay

Anchorage-independent growth is a characteristic of tumorigenic cell lines. Human tumor cells are suspended in growth medium containing 0.3% agarose and an indicated concentration of a farnesyl transferase inhibitor. The solution is overlayed onto growth medium solidified with 0.6% agarose containing the same concentration of farnesyl transferase inhibitor as the top layer. After the top layer is solidified, plates are incubated for 10–16 days at 37° C. under 5% $CO_2$ to allow colony outgrowth. After incubation, the colonies are stained by overlaying the agar with a solution of MTT (3-[4,5-dimethylthiazol-2-yl]-2,5-diphenyltetrazolium bromide, Thiazolyl blue) (1 mg/mL in PBS). Colonies can be counted and the $IC_{50}$'s can be determined.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples
EXAMPLE A
Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B
Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

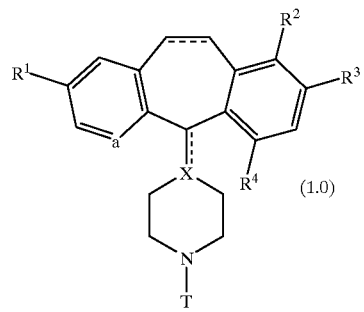

or a pharmaceutically acceptable salt or solvate thereof, wherein:

a represents N;

$R^1$ and $R^3$ are the same or different and each represents halo;

$R^2$ and $R^4$ are each independently selected from H and halo, provided that at least one of $R^2$ and $R^4$ is H;

each dotted line (---) represents an optional bond;

X is C when the optional bond to X is present, or CH when the optional bond to X is absent;

T is a substituent selected from:

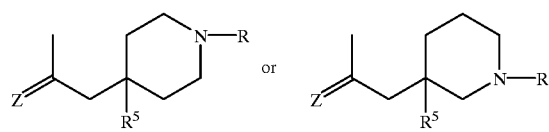

Z represents O;

R represents $-SO_2R^{10}$;

$R^5$ represents alkyl, aryl, arylalkyl, heteroaryl, heteroarylalkyl, cycloalkyl, $OR^{12}$, $NR^{12}H$, SH, $SR^{12}$, $SOR^{12}$ (where $R^{12}$ is not H), or $SO_2R^{12}$ (where $R^{12}$ is not H); and $R^{10}$ represents alkyl;

$R^{12}$ is selected from H, alkyl, aryl, aralkyl, heteroaryl, heteroarylalkyl, or heterocycloalkyl.

2. The compound of claim 1 having the formula:

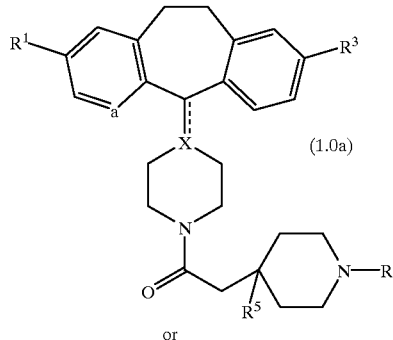

-continued

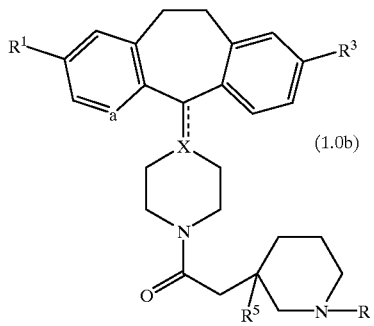

wherein $R^1$, $R^2$, $R^3$, $R^4$, a, X, $R^5$, R and the dotted lines are as defined in claim 1.

3. The compound of claim 1 having the formula:

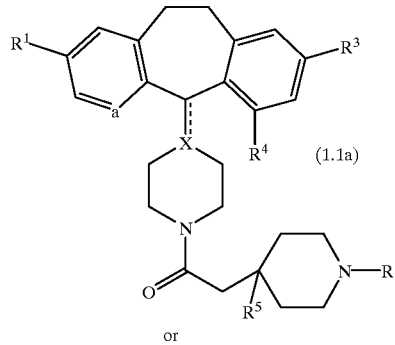

or

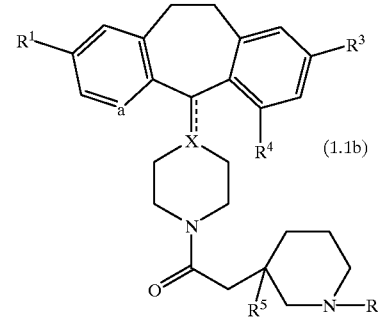

wherein $R^1$, $R^2$, $R^3$, $R^4$, a, X, $R^5$, R and the dotted lines are as defined in claim 1.

4. The compound of claim 1 having the formula:

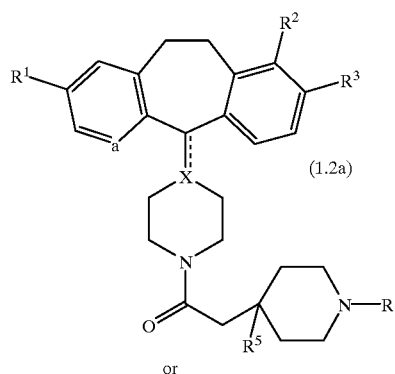

or

-continued

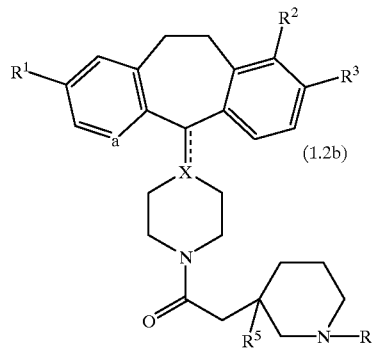

wherein $R^1$, $R^2$, $R^3$, $R^4$, a, X, $R^5$, R and the dotted lines are as defined in claim 1.

5. The compound of claim 1 having the formula:

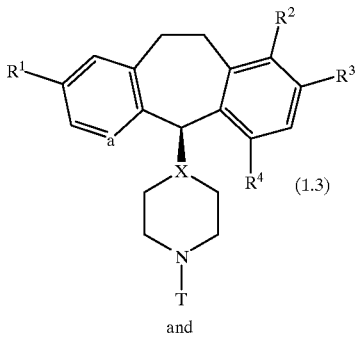

and

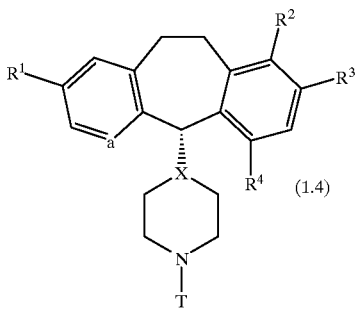

wherein $R^1$, $R^2$, $R^3$, $R^4$, a and T are as defined in claim 1 and X is CH.

6. The compound of claim 2 wherein $R^1$ is bromo, $R^3$ is chloro, a is N, and R and $R^5$ are as defined in claim 1.

7. The compound of claim 3 wherein $R^1$ is bromo, $R^3$ is chloro, $R^4$ is bromo, a is N, and R and $R^5$ are as defined in claim 1.

8. The compound of claim 4 wherein $R^1$ is bromo, $R^2$ is bromo, $R^3$ is chloro, a is N, and R and $R^5$ are as defined in claim 1.

9. The compound of claim 5 wherein $R^1$ is bromo, $R^2$ is H or bromo, $R^3$ is chloro, $R^4$ is H or bromo, a is N, and $R^5$ and R are as defined in claim 1.

10. The compound of claim 9 wherein T is selected from:

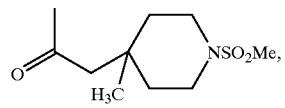

-continued

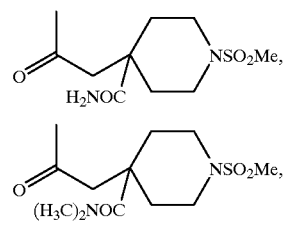

11. A method of treating tumor cells in a human by inhibition of farnesyl protein transferase wherein the tumor cells are pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumors cells, breast tumor cells and prostate tumor cells comprising administering to the human in need thereof a farnesyl protein transferase inhibiting amount of a compound of claim 1.

12. A method of inhibiting farnesyl protein transferase in a human comprising the administration to the human in need thereof a farnesyl protein transferase inhibiting amount of the compound of claim 1.

13. A pharmaceutical composition comprising an effective amount of compound of claim 1 in combination with a pharmaceutically acceptable carrier.

14. A compound of the formula:

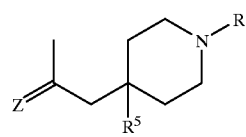

or a pharmaceutically acceptable salt or solvate thereof, wherein:

a represents N;

$R^1$ and $R^3$ are the same or different and each represents halo;

$R^2$ and $R^4$ are each independently selected from H and halo, provided that at least one of $R^2$ and $R^4$ is H;

X is CH;

T is a substituent selected from:

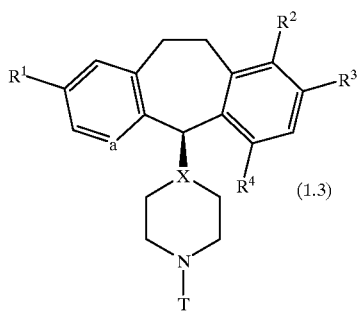

Z represents O;
R represents $-SO_2R^{10}$;
$R^5$ represents alkyl; and
$R^{10}$ represents alkyl.

15. A compound of the formula:

16. A method of treating tumor cells in a human by inhibition of farnesyl protein transferase wherein the tumor cells are pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumors cells, breast tumor cells and prostate tumor cells comprising administering to the human in need thereof a farnesyl protein transferase inhibiting amount of a compound of claim 14.

17. A pharmaceutical composition comprising an effective amount of compound of claim 14 in combination with a pharmaceutically acceptable carrier.

18. A method of treating tumor cells in a human by inhibition of farnesyl protein transferase wherein the tumor cells are pancreatic tumor cells, lung cancer cells, myeloid leukemia tumor cells, thyroid follicular tumor cells, myelodysplastic tumor cells, epidermal carcinoma tumor cells, bladder carcinoma tumor cells, colon tumors cells, breast tumor cells and prostate tumor cells comprising administering to the human in need thereof a farnesyl protein transferase inhibiting amount of a compound of claim 15.

19. A pharmaceutical composition comprising an effective amount of compound of claim 15 in combination with a pharmaceutically acceptable carrier.

* * * * *